US005885786A

United States Patent [19]
Cabot

[11] Patent Number: 5,885,786
[45] Date of Patent: Mar. 23, 1999

[54] METHODS FOR SCREENING OF SUBSTANCES FOR INHIBITION OF MULTIDRUG RESISTANCE

[75] Inventor: Myles Cabot, Santa Monica, Calif.

[73] Assignee: John Wayne Cancer Institute, Santa Monica, Calif.

[21] Appl. No.: 636,513

[22] Filed: Apr. 19, 1996

[51] Int. Cl.$^6$ .................................................. G01N 33/53
[52] U.S. Cl. ...................... 435/7.21; 435/7.23; 435/7.24; 435/7.95; 436/71; 436/161; 436/162; 436/174; 436/503; 436/518; 436/527
[58] Field of Search .................................. 435/4, 7.1, 7.2, 435/7.21, 7.23, 7.92, 7.95, 7.24; 436/501, 503, 518, 64, 63, 71, 524, 527, 174, 161, 162

[56] References Cited

PUBLICATIONS

Marcus, Molecular Immunology, 21(11):1083–1091, 1984.
McKibbin et al, Biochimica et Biophysica Acta, 958:235–246, 1988.
Dyatlovitskaya, E.V., "Sphingolipids and Malignant Growth", *Biochemistry*, 60(6)629–633, 1995.
Holleran, et al., "Characterization of cellular lipids in doxorubicin–sensitive and –resistant P388 mouse leukemia cells", *Cancer Chemotherapy and Pharmacology*, 17(1):11–15, 1986.
Lavie, et al., "Agents that Reverse Multidrug Resistance, Tamoxifen, Verapamil, and Cyclosporin A, Block Glycosphingolipid Metabolism by Inhibiting Ceramide Glycosylation in Human Cancer Cells", *The Journal of Biological Chemistry*, 278(3):1682–1687, 1997.
International Search Report dated Sep. 5, 1997.
Abe et al., "Metabolic Effects of Short–Chain Ceramide and Glucosylceramide on Sphingolipids and Protein Kinase C," *Eur. J. Biochem.*, 210:765–773, 1992.
Abe et al., "Structural and Stereochemical Studies of Potent Inhibitors of Glucosylceramide Synthase and Tumor Cell Growth," *Journal of Lipid Research*, 36:611–621, 1995.
Breimer et al., "The Specific Glycosphingolipid Composition of Human Ureteral Epithelial Cells," *J. Biochem.*, 98(5):1169–1180, 1985.
Cabot et al., "Tamoxifen Retards Glycosphingolipid Metabolism in Human Cancer Cells," FEBS Letters, 00:1–3, 1996.
Callaghan and Higgins, "Interaction of Tamoxifen with the Multidrug Resistance P–Glycoprotein," *British Journal of Cancer*, 71:294–299, 1995.
Cheresh et al., "Localization of the Gangliosides GD$_2$ and GD$_3$ in Adhesion Plaques and on the Surface of Human Melanoma Cells," *Proc. Nat'l. Acad. Sci. USA*, 81:5767–5771, Sep., 1984.
Escriba et al., "Role of Membrane Lipids on the Interaction of Daunomycin with Plasma Membranes from Tumor Cells: Implications in Drug–Resistance Phenomena," *Biochemistry*, 29:7275–7282, 1990.

Ford et al., "Structural Features Determining Activity of Phenothiazines and Related Drugs for Inhibition of Cell Growth and Reversal of Multidrug Resistance," *Molecular Pharmacology*, 35:105–115, 1988.
Chatterjee and Harris, "Reversal of Acquired Resistance to Adriamycin in CHO Cells by Tamoxifen and 4–Hydroxy Tamoxifen: Role of Drug Interaction with Alpha 1 Acid Glycoprotein," *Br. J. Cancer*, 62:712–717, 1990.
Ikushima et al., "Effects of Polyunsaturated Fatty Acids on Vincristine–Resistancein Human Neuroblastoma Cells," *AntiCancer Research*, 11:1215–1220, 1991.
Inokuchi et al., "Antitumor Activity Via Inhibition of GlycosphingolipidBiosynthesis," *Cancer Letters*, 38:23–30, 1987.
Inokuchi et al., "Effects of D–Threo–PDMP, An Inhibitor of Glucosylceramide Synthetase, on Expression of Cell Surface Glycolipid Antigen and Binding to Adhesive Proteins by B16 Melanoma Cells," *Journal of Cellular Physiology*, 141:573–583, 1989.
Inokuchi and Radin, "Preparation of the Active Isomer of 1–Phenyl–2–Decanoylamino–3–Morpholino–1–Propanol, Inhibitor of Murine Glucocerebroside Synthetase," *Journal of Lipid Research*, 28:565–571, 1987.
Jaffrézou et al., "Inhibition of Lysosomal Acid Sphingomyelinaseby Agents Which Reverse Multidrug Resistance," *Biochimica et Biophysica Acta*1266:1–8, 1995.
Kajiji et al., "Structurally Distinct MDR Modulators Show Specific Patterns of Reversal Against P–Glycoproteins Bearing Unique Mutations at Serine," *Biochemistry*, 33(17):5041–5048, 1994.
Kirk et al., "Reversal of P–Glycoprotein–MediatedMultidrug Resistance By Pure Anti–Oestrogens and Novel Tamoxifen Derivatives," *Biochemical Pharmacology*, 48(2):277–285, 1994.
Lavie et al., "Accumulation of Glucosylceramides in Multidrug–Resistant Cancer Cells," *The Journal of Biological Chemistry*, 271(32):19530–19536, 1996.
Le Moyec et al., "Proton Nuclear Magnetic Resonance Spectroscopy Reveals Cellular Lipids Involved in Resistance to Adriamycin and Taxol by the K562 Leukemia Cell Line," *Cancer Research*, 56:3461–3467, 1996.
Lloyd et al., "Cell Surface Accessibility of Individual Gangliosides in Malignant Melanoma Cells to Antibodies Is Influenced by the Total Ganglioside Composition of the Cells," *Cancer Research*, 52:4948–4953, Sep. 1992.
Madhavi and Das, "Effect of n–6 and n–3 Fatty Acids on the Survival of Vincristine Sensitive and Resistant Human Cervical Carcinoma Cells In Vitro," *Cancer Letters*, 84:31–41, 1994.

(List continued on next page.)

*Primary Examiner*—Patricia Duffy
*Attorney, Agent, or Firm*—Arnold, White & Durkee

[57] ABSTRACT

The present invention provides for the screening of candidate substances to identify active compounds that inhibit multidrug resistance (MDR). The expression of glucosylceramides has been determined to be a marker of MDR. By measuring glucosylceramide expression in cells exhibiting MDR, and the reduction in glucosylceramide levels in the presence of a candidate substance, the present invention provides for the identification of MDR inhibitory compounds.

22 Claims, 24 Drawing Sheets

OTHER PUBLICATIONS

Peterson et al., "Ganglioside Composition of Malignant and Actinomycin D–Resistant NonMalignant Chinese Hamster Cells," *Biochemical Pharmacology*, 28:579–582, 1979.

Ramu et al., "Circumvention of Multidrug–Resistancein P388 Cells is Associated With a Rise in the Cellular Content of Phosphatidylcholine," *Biochemical Pharmacology*, 41(10):1455–1461, 1991.

Rani et al., "Cell Cycle Arrest Induced by an Inhibitor of Glucosylceramide Synthase," *The Journal of Biological Chemistry*, 270(6):2859–2867, 1995.

Rosenwald and Pagano, "Effects of the Glucosphingolipid Synthesis Inhibitor, PDMP, on Lysosomes in Cultured Cells," *Journal of Lipid Research*, 35:1232–1240, 1994.

Sasagasako et al., "Glucosylceramide and Glucosylsphingosine Metabolism in Cultured Fibroblasts Deficient in Acid β–Glucosidase Activity," *J. Biochem.*, 115:113–119, 1994.

Schwarzmann et al., "Demonstration of Direct Glycosylation of Nondegradable Glucosylceramide Analogs in Cultured Cells," *The Journal of Biological Chemistry*, 270(36):21271–21276, 1995.

Thurin et al., "GD2 Ganglioside Biosynthesis is a Distinct Biochemical Event in Human Melanoma Tumor Progression," *FEBS*, 208(1):17–22, 1986.

Urbatsch and Seniro, "Effects of Lipids on ATPase Activity of Purified Chinese Hamster P–Glycoprotein," *Archives of Biochemistry and Biophysics*, 316(1):135–140, 1995.

Warnock et al., "Transport of Newly Synthesized Glucosylceramide to the Plasma membrane by a Non–Golgi Pathway," Proc. Natl. Acad. Sci., 91:2708–2712, 1994.

Wheeler et al., "Membrane alterations Associated with Progressive Adriamycin Resistance," *Biochemical Pharmacology*, 31(16):2691–2693, 1982.

Wurz et al., "Targeting Chemosensitizing Doses of Toremifene Based on Protein Binding," *Cancer Chemother Pharmacol.*, 31:412–414, 1993.

Ramu et al. "Circumvention of Multidrug–Resistancein P388 Cells is Associated with a Rise in the Cellular Content of Phosphatidylcholine," *Biochemical Pharmacology*, 41(10):1455–1461, 1991.

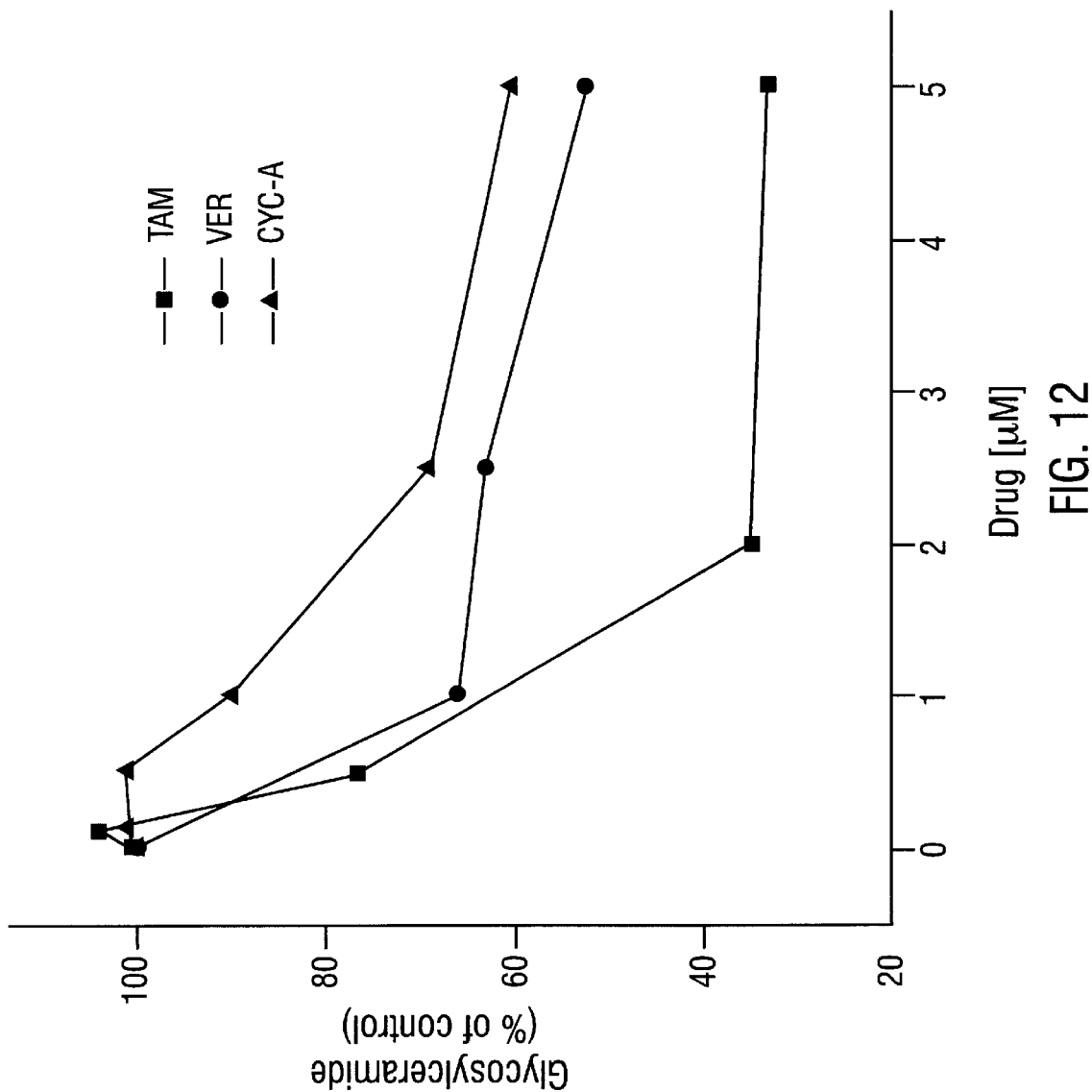

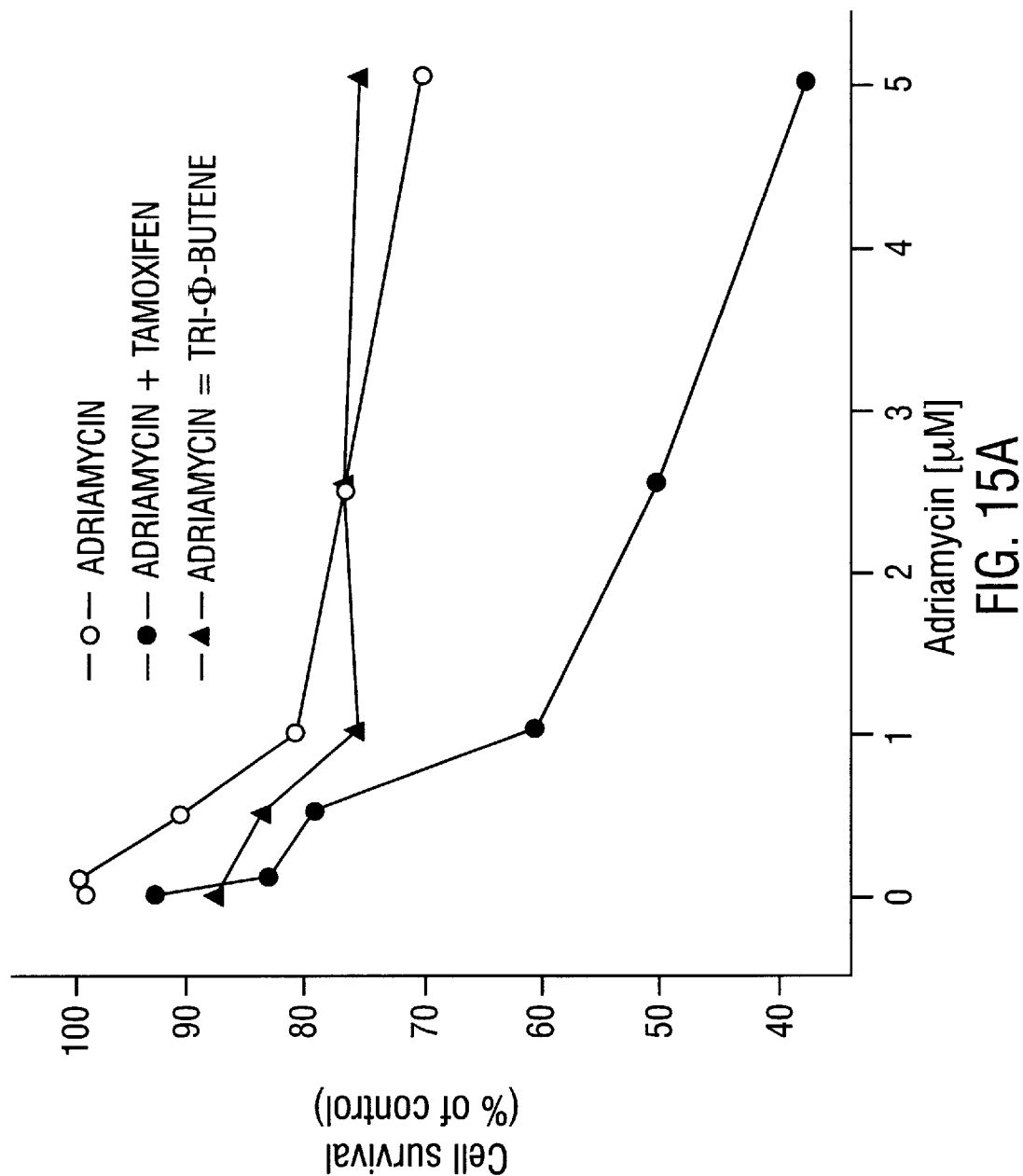

METHODS FOR SCREENING OF SUBSTANCES FOR INHIBITION OF MULTIDRUG RESISTANCE

BACKGROUND OF THE INVENTION

1. Field of the Invention

The present invention relates generally to the fields of detection and treatment of cancer. More particularly, it concerns the detection and treatment of multidrug resistant cancers by screening for phingoglycolipids, including glycosylceramides, cerebrosides and gangliosides.

2. Description of Related Art

Clinical resistance to anticancer agents is the principal reason for treatment failure in patients with cancer (Gottesman, 1993). The best-characterized type of drug resistance is classic multidrug resistance (MDR), exhibiting intrinsic resistance to multiple drugs upon primary exposure to a single drug (i.e., vinblastine, adriamycin, taxol, actinomycin D) (Bradley et al., 1988).

Among the multiple biochemical and molecular mechanisms associated with MDR, overexpression of P-glycoprotein (P-gp), a plasma-membrane protein proposed to act as an ATP-driven drug efflux pump, is best studied (Volm et al., 1993; Bradley and Ling, 1994). However, the physiologic function and mechanisms of action of P-gp are largely unknown. Moreover, widespread occurrence of drug resistance in human lung tumors (Cole et al., 1992), which is unrelated to overexpression of P-gp, indicates the existence of additional resistance mechanisms.

The multifactorial nature of MDR is exemplified by a wide array of other biochemical changes including alterations in membrane fluidity and structure (Bradley and Ling, 1994), elevated glutathione S-transferase activity (Bradley and Ling, 1994; Volm et al., 1993), down-regulation of topoisomerase II (Volm et al., 1993), increased phospholipase D activity (Welsh et al., 1994), and elevated transcription of c-fos, c-myc and c-H-ras (Chin et al., 1992; Volm et al., 1993, Sabbatini et al., 1994).

Several associations have been made regarding the role of lipids in drug partitioning, drug transport and drug retention. Reports have shown that P-gp ATPase-activity is dependent on the lipid environment (Doige et al., 1993), and that lipids interact with P-gp substrates (Wadkins and Houghton, 1993; Wright et al., 1985; May et al., 1988; Peterson et al., 1983). Early studies investigated lipid composition of MDR cells as a general feature that may be influential (Holleran et al., 1986; Ramu et al., 1984; May et al., 1988). Differences in lipid composition of drug-sensitive and -resistant cells have been reported, but these were mainly confined to triglycerides, fatty alcohols, and ether lipids, with minor changes in sphingomyelin and phosphatidylcholine (Ramu et al., 1984; Welsh et al., 1994; Wright et al., 1985).

The ganglioside composition of daunorubicin-resistant, vincristine-resistant, and drug-sensitive cells has been examined. Whereas diversity in ganglioside composition was revealed, no definitive correlation to drug resistance was demonstrated (Biedler et al., 1986; Peterson et al., 1983). In other studies, the levels of four major lipid classes, including gangliosides, in doxorubicin-sensitive and -resistant P388 cells, were examined, and no differences in lipid composition were noted (Holleran et al., 1986).

Circumvention of MDR, via re-sensitizing of cells to drug insult, carries major clinical importance (Bradley et al., 1988; Gottesman, 1993). Tsuruo and coworkers showed that a battery of different agents inhibit MDR, rendering cells sensitive to chemotherapy (Tsuruo et al., 1981). Included in this category are the calcium channel blockers verapamil and SR33557 (Tsuruo et al., 1981; Jaffrezou et al., 1991), antiarrhythmic agents like quinidine (Solary et al., 1991), the immunosuppressant cyclosporin A (Slater et al., 1986; Solary et al., 1991), and the anticancer drug tamoxifen (Nayfield, 1995; Kirk et al., 1994).

The mechanism by which these drugs promote influence on MDR cells is thought to be via direct binding of the drug to P-gp with subsequent inhibition of pump activity (Yusa and Tsuruo, 1989; Callaghan and Higgins, 1995). In addition, drugs may exercise effects by modulating other cellular components that subsequently regulate P-gp. For example, selective expression of protein kinase C (PKC) isozymes was correlated with MDR (Blobe et al., 1993), and studies have suggested that P-gp activity can be regulated by PKC (Blobe et al., 1993; Gupta et al., 1996).

Recently, a correlation was demonstrated between inhibition of PKC activity by safingol, and reversal of MDR in MCF-7-doxorubicin resistant cells (Sachs et al., 1995). Also, the calcium channel blocker, SR33557, elicits inhibition of acid sphingomyelinase, and an increase in cellular sphingosine levels which may be correlated with its ability to reverse MDR in P388-adriamycin resistant cells (Jaffrezou et al., 1991). Other work examined a multitude of MDR-circumventing drugs revealing a correlation between inhibition of cellular acid sphingomyelinase activity and tempering of MDR (Jaffrezou et al., 1995).

SUMMARY OF THE INVENTION

The present invention describes, for the first time, a distinct lipid profile in MDR cells, as compared to chemosensitive cells, and discloses methods of sensitizing MDR cells to chemotherapeutic agents through a previously unknown mechanism. More specifically, the present invention demonstrates that particular sphingoglycolipids are associated with particular MDR cells. Surprisingly, the synthesis of theses lipids is blocked by a myriad of drugs previously used to treat MDR cancers. A clear correlation between reduction in cellular lipid content and sensitization of MDR cells to anticancer agent toxicity is, for the first time, established.

Accordingly, there is provided a method for determining the multidrug resistance of a cell comprising the steps of (i) measuring the level of at least one sphingoglycoslipid in said cell; and (ii) comparing the level of said sphingoglycolipid with the level observed in normal cells, wherein the elevation of the level of said sphingoglycolipid indicates multidrug resistance.

The sphingoglycolipid preferably is a glycosylceramide, and the glycosylceramide may be selected from the group consisting of N-tetracosanoyl (lignoceroyl) monoglycosylceramide, N-tetracosanoyl (nervonoyl) monoglycosylceramide, N-docosanoyl monoglycosylceramide and N-linoleoyl monoglycosylceramide.

The method of measuring may comprise chromatographic separation of the components of said cell, and the chromatographic separation may comprise thin layer chromatography, gas chromatography, high performance liquid chromatography, paper chromatography, affinity chromatograph or supercritical flow chromatography.

The method of measuring also may comprise contacting the components of said cell with a first antibody that binds immunologically to an epitope on said sphingoglycolipid. This particular method may comprise contacting the antibody-component mixture with a second antibody that binds immunologically to said first antibody.

In preferred embodiments, the cell is a cancer cell. For example, a cancer cell may be a lymphoma, melanoma, sarcoma, leukemia, retinoblastoma, hepatoma, myeloma, glioma, mesothelioma and carcinoma.

There also is provided a method of determining inhibition of multidrug resistance comprising the steps of (i) providing a multidrug resistant cell, wherein the elevated level of at least one sphingoglycolipid in said cell indicates multidrug resistance; (ii) contacting said cell with a candidate substance; (iii) incubating said cell; (iv) measuring the level, in said cell, of said sphingoglycolipid; and (v) comparing the level of said sphingoglycolipid in the cell of step (iii) with the level of said sphingoglycolipid in the cell of step (i), wherein a decrease in the level of said sphingoglycolipid in the cell of steip (iii) indicates that said candidate substance is an inhibitor of the multidrug resistance.

Again, the sphingoglycolipid preferably is a glycosylceramide, and the glycosylceramide may be selected from the group consisting of N-tetracosanoyl (lignoceroyl) monoglycosylceramide, N-tetracosanoyl (nervonoyl) monoglycosylceramide, N-docosanoyl monoglycosylceramide and N-linoleoyl monoglycosylceramide.

The method of measuring may comprise chromatographic separation of the components of said cell, and the chromatographic separation may comprise thin layer chromatography, gas chromatography, high performance liquid chromatography, paper chromatography, affinity chromatograph or supercritical flow chromatography.

The method of measuring also may comprise contacting the components of said cell with a first antibody that binds immunologically to an epitope on said sphingoglycolipid. This particular method may comprise contacting the antibody-component mixture with a second antibody that binds immunologically to said first antibody.

In preferred embodiments, the cell is a cancer cell. For example, a cancer cell may be a lymphoma, melanoma, sarcoma, leukemia, retinoblastoma, hepatoma, myeloma, glioma, mesothelioma and carcinoma.

In yet another embodiment, there is provided a purified antibody that binds to a glycosylceramide. The purified antibody may be immunologically reactive with a glycosylceramide selected from the group consisting of N-tetracosanoyl (lignoceroyl) monoglycosylceramide, N-tetracosanoyl (nervonoyl) monoglycosylceramide, N-docosanoyl monoglycosylceramide and N-linoleoyl monoglycosylceramide.

In still yet another embodiment, there is provided a method of sensitizing a cell to a chemotherapeutic agent comprising administering to said cell a compound that inhibits the level of at least one sphingoglycolipid in said cell. The preferred cell is a multidrug resistant cell, and the preferred sphingoglycolipid is a glycosylceramide. The drug may be tamoxifen, verapimil or cyclosporin A.

In still yet another embodiment, there is provided a method of killing a cell by administering to cells a compound capable of inhibiting sphingoglycolipid synthesis and a chemotherapeutic agent. The preferred cell is a multidrug resistant cell, and the preferred sphingoglycolipid is a glycosylceramide. The drug may be tamoxifen, verapimil or cyclosporin A.

In still yet another embodiment, there is provided an inhibitor of sphingoglycolipid synthesis identified according to a method comprising the steps of (i) providing a multidrug resistant cell, wherein the elevated level of at least one sphingoglycolipid in said cell indicates multidrug resistance; (ii) contacting said cell with a candidate substance; (iii) incubating said cell; (iv) measuring the level, in said cell, of said sphingoglycolipid; and (v) comparing the level of said sphingoglycolipid in the cell of step (iii) with the level of said sphingoglycolipid in the cell of step (i), wherein a decrease in the level of said sphingoglycolipid step indicates that the compound is an inhibitor of the multidrug resistance.

The sphingoglycolipid preferably is a glycosylceramide, and the glycosylceramide may be selected from the group consisting of N-tetracosanoyl (lignoceroyl) monoglycosylceramide, N-tetracosanoyl (nervonoyl) monoglycosylceramide, N-docosanoyl monoglycosylceramide and N-linoleoyl monoglycosylceramide.

The method of measuring may comprise chromatographic separation of the components of said cell, and the chromatographic separation may comprise thin layer chromatography, gas chromatography, high performance liquid chromatography, paper chromatography, affinity chromatograph or supercritical flow chromatography.

The method of measuring also may comprise contacting the components of said cell with a first antibody that binds immunologically to an epitope on said sphingoglycolipid. This particular method may comprise contacting the antibody-component mixture with a second antibody that binds immunologically to said first antibody.

In preferred embodiments, the cell is a cancer cell. For example, a cancer cell may be a lymphoma, melanoma, sarcoma, leukemia, retinoblastoma, hepatoma, myeloma, glioma, mesothelioma and carcinoma.

Finally, there are provided methods for the screening of multidrug resistant cells for sphingoglycolipids that are present in amounts that differ from the amounts found in drug sensitive cells of the same type. Typically, the multidrug resistant cell will be cancer cells. The method by which the lipid content of the cell is measured may comprise chromatographic separation of the components of said cell, and the chromatographic separation may comprise thin layer chromatography, gas chromatography, high performance liquid chromatography, paper chromatography, affinity chromatograph or supercritical flow chromatography.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: Route of glucosylceramide formation. Inhibitors used in this study are shown in black boxes. FIG. 1B: General molecular structure of glucosylceramide.

(FIG. 7A) upper TLC band (lipid-1); (FIG. 7B) lower TLC band (lipid-2).

FIG. 11: A Autoradiography. Cells, preincubated for 30 min with 5.0 $\mu$M of each of the indicated drugs, were then labeled with 1.0 $\mu$Ci/ml [$^3$H]palmitic acid in medium containing the indicated drugs for 24 h. For autoradiography equal aliquots by volume of total lipid extract were applied to TLC plates. Glc-cer, glycosylceramide; PE, phosphatidylethanolamine; PC, phosphatidylcholine; SM, sphingomyelin; Con, control; Tam, tamoxifen; Tri-φ-butene, triphenylbutene; Ver, verapamil; Cyc-A, cyclosporin A. FIG. 11B: Quantitation of glycosylceramide levels in cells following treatment with drugs. [$^3$H]Glycosylceramide, visualized in panel A, was quantitated as described in the legend to FIG. 9. Each value represents mean±SEM of determinations from three separate experiments.

FIG. 12. Influence of Increasing Concentrations of Tamoxifen, Verapamil, and Cyclosporin A on Glycosylceramide Metabolism. MCF-7-AdrR cells were labeled with 1.0 $\mu$Ci/ml [$^3$H]palmitic acid for 24 h in the presence of drugs at the indicated concentrations. [$^3$H]Glycosylceramide was quantitated as described in the legend to FIG. 9. Results represents the mean±SEM of determinations from three separate experiments.

FIG. 14: A Influence of tamoxifen on ceramide synthesis. The experiment was conducted as described in the legend to FIG.

13. Aliquots of the total lipid extract were based-hydrolyzed as described in Example I, separated by TLC using solvent system IV, and the resolved [$^3$H]ceramide was quantitated by liquid scintillation spectrometry. Results are the mean±SEM of duplicate determinations from two separate experiments. FIG. 14B: Effect of tamoxifen on glycosylation of C$_6$-ceramide. Cells, in 100×20 mm culture dishes, were preincubated without or with 5.0 μM tamoxifen for 30 min, followed by incubation without or with 5.0 μM C$_6$-ceramide:BSA (prepared at a 1:1 molar ratio) for an additional 30 min. Cells were labeled thereafter with 1.0 μCi/ml [$^3$H]galactose for 24 h. [3H]Galactose uptake was determined and found to be similar in all experimental points (1.0×10$^6$ cpm/dish). The total extracted lipid was applied to TLC separation and [$^3$H]glycosphingolipids were analyzed as described in the legend to FIG. 10. The autoradiography of a representative chromatogram is shown.

FIG. 15A and FIG. 15B. Correlation Between MDR Reversal and Reduction in Glycosylceramide Levels in MCF-7-AdrR Cells. FIG. 15A: Influence of tamoxifen on chemo-susceptibility of MDR cells to adriamycin. MCF-7-AdrR cells were exposed to 0–5.0 μM adriamycin for 72 h in the presence or absence of tamoxifen or triphenylbutene (5.0 μM). Cell survival was determined using a cell proliferation assay as described in Example I. Each point represents the mean of six replicate determinations from a representative experiment. FIG. 15B: Glycosylceramide levels in MDR Cells following drug treatment. MCF-7-AdrR cells, preincubated without or with adriamycin (2.5 μM), tamoxifen (5.0 μM), triphenylbutene (5.0 μM), or the indicated combination of drugs, were labeled with 2.0 μCi/ml [$^3$H] serine for 48 h, similar with the experiment described in panel A. [$^3$H]Glycosylceramide was quantitated as described in the legend to FIG. 9. In order to avoid differences in [$^3$H]glycosylceramide values which account for cell death, the same amount of total radioactive lipid from each sample was applied to TLC separation. Results are from one of two experiments that gave similar values.

FIG. 16A: Effect of PPMP on cellular glycosylceramide levels. MCF-7-AdrR cells were labeled with 2.0 μCi/ml [$^3$H]serine for 24 h in the presence of the indicated PPMP concentrations. [$^3$H]Glycosylceramide was quantitated as described in the legend to FIG. 9. Results are from one of two experiments that gave similar values. FIG. 16B: Effect of PPMP in combination with adriamycin on MCF-7-AdrR cell survival. Cells were exposed to increasing concentrations of adriamycin for 72 h in the presence or absence of PPMP (5.0 μM). Cell survival was determined by cell proliferation assay as described in Example I. Each point represent the mean of six replicate determinations from a representative experiment.

DETAILED DESCRIPTION OF THE INVENTION

Figure 1A:
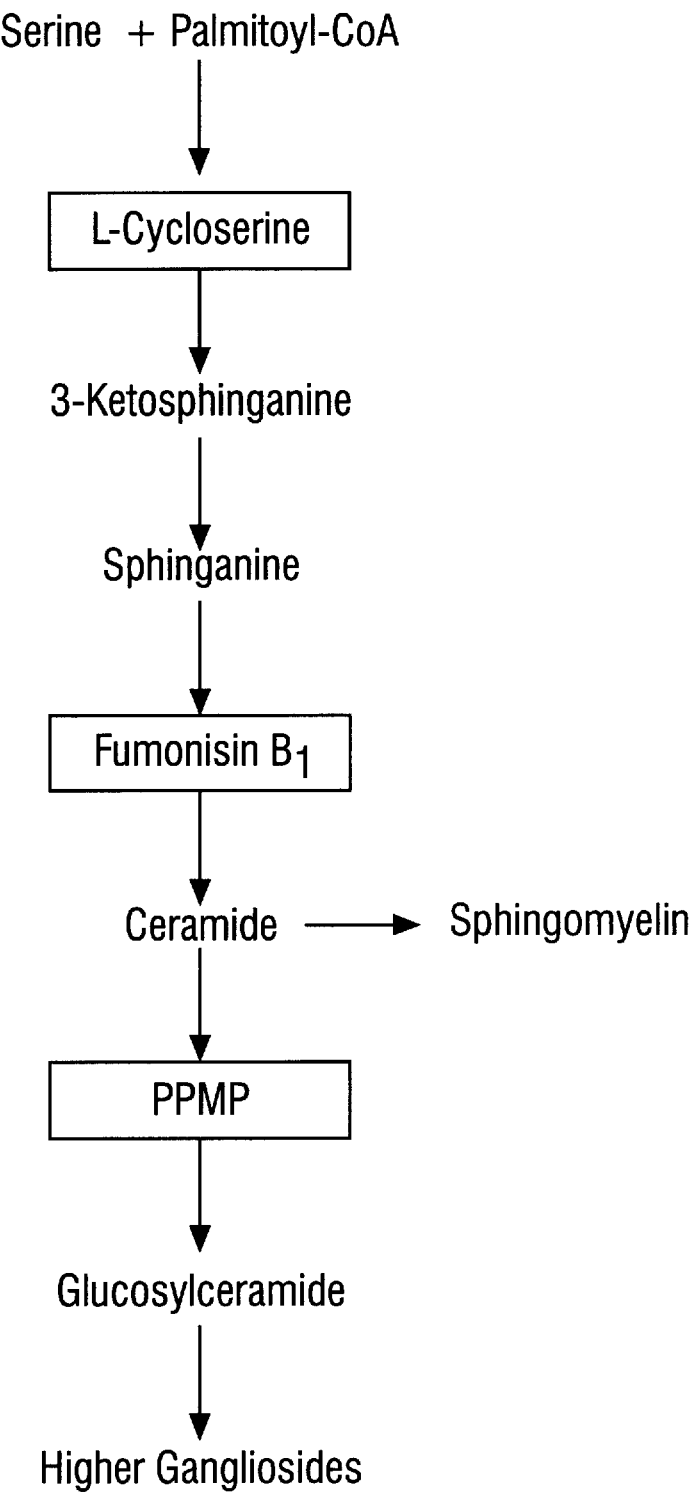
FIG. 1A and FIG. 1B. Biosynthesis and structure of glucosylceramide.

The present invention provides new methods for the diagnosis and treatment of multidrug resistant (MDR) cancers. For example, the invention provides methods for diagnosing multidrug resistance by testing for glycolipids such as glycosylceramides, cerebrosides and gangliosides. Further, the invention also provides methods for sensitizing multidrug resistant cancer cells by inhibiting the synthesis of glycolipids. Both of these aspects of the invention stem from the original observation that certain glycolipids are synthesized in varying levels in MDR cells and, further, that certain chemical agents, such as tamoxifen, can block the synthesis of these lipids. Thus, in combination with antineoplastic agents, the blocking drugs provide increased sensitivity of multidrug resistant cancers to standard chemotherapeutics.

Sphingoglycolipids

Sphingoglycolipids are demonstrated to have a crucial role in cell growth (Rani et al., 1995) and survival (Furuya et al., 1995), and in escape from onset of apoptosis (Nakamura et al., 1996). Moreover, data from several studies has linked inhibition of sphingoglycolipid synthesis to an array of cellular dysfunctions (Abe et al., 1995; Harel and Futerman, 1993; Hannun and Bell, 1989; Yan et al., 1995; Furuya et al., 1995).

Sphingomyelin, cerebrosides, and gangliosides are important cell membrane constituents (Sweeley, 1985). The glycosphingolipids are a uniquely important sub-group with obligatory functions in cell proliferation (Hakamori, 1993; Rani et al., 1995), neuronal growth (Schwarz et al., 1995; Furuya et al., 1995), cell transformation (Hakamori, 1993) and in tumor progression (Thurin et al., 1986). The major cellular glycosphingolipids are glycosylceramides, lactosylceramides, and gangliosides. Glycosphingolipids have been suggested to play an important role in cell growth (Rani et al., 1995). Furthermore, sphingoglycolipid synthesis has been linked to an array of cellular dysfunctions (Abe et al., 1995; Harel and Futerman, 1993; Hannun and Bell, 1989; Yan et al., 1995; Furuya et al., 1995).

Changes in expression of various glycolipids on the cell surface have been correlated with mechanisms of acquiring and maintaining cancer phenotype and tumor progression (Hakomori, 1981; Morton et al., 1994). For example, human melanomas express GD2 ganglioside, and as melanoma cell tumorigenesis progresses, the level of GD2 increases (Thurin et al., 1986). This increase may be correlated with metastatic potential, as GD2 has been implicated in the attachment of melanoma cells to solid substrata (Cheresh et al., 1984).

A novel sialylated fucosyl sphingoglycolipid has been characterized in chronic myelogenous leukemia cells (Fukuda et al., 1986), and occurrence of another ganglioside, GD1α, has been associated with rat ascites hepatoma AH 7974F cells (Taki et al., 1986). Earlier studies have endeavored to identify differences between sphingolipid synthesis and composition in drug-sensitive and drug-resistant cells. Differences in lipid composition of doxorubicin-sensitive and -resistant P388 cells were reported, but were mainly confined to triglycerides with minor changes in sphingomyelin and phosphatidylcholine in drug-resistant cells (Ramu et al., 1984).

Biedler and coworkers (Biedler et al., 1983), examined ganglioside composition of daunorubicin-resistant, vincristine-resistant, and drug-sensitive control cells. Although differences in ganglioside composition were found, there was no definitive correlation with drug resistance. In another study, the levels of four major lipid classes, including gangliosides, in doxorubicin-sensitive and -resistant P388 cells were examined (Holleran et al., 1986). No differences in lipid composition were noted (Holleran et al., 1986).

The contribution of glycolipids may be important for the capacity of cells to survive a hostile environment (Furuya et al., 1995, Nakamura et al., 1996, Yan et al., 1995). Interestingly, drugs that inhibit sphingoglycolipid synthesis provoke cytotoxic actions on cells. For example, recent work showed that 3'-azidothymidine altered sphingoglycolipid metabolism in K562 erytiroleukemia cells, an effect which may be related to cytotoxicity (Yan et al., 1995).

Glycosylceramides

Glycosylceramides are one class of sphingoglycolipids. For the purposes of the present invention, glycosylceramides are sugar lipids, including sugar moieties of galactose, glucose, lactose and lycosyl ceramide. Glycosylceramide serves as a precursor and is the degradation product of all glycosphingolipids. The enzyme that catalyzes the synthesis of glucosylceramide, UDP-glucose:ceramide glucosyltransferase, is central in sphingoglycolipid metabolism. Specific inhibition of this enzyme activity by PPMP, a synthetic inhibitor that acts as a ceramide analog, unraveled a diversity of physiological processes affected by depleting cells of glycosylceramide and higher glycosphingolipids (Abe et al., 1995; Inokuchi et al., 1987; Rani et al., 1995; Schwarz et al., 1995). In addition, deficiencies in glucosyltransferase are the cause of Gaucher's disease, a malady belonging to a group of inherited lysosomal sphingolipidoses (Nilsson and Svennerholm, 1982). Ceramide is suggested to serve as a second messenger for programmed cell death (Obeid et al., 1993).

Glycosylceramides play a role in cell growth (Hannun and Bell, 1989; Schwarz et al., 1995, Rani et al., 1995), differentiation (Hannun and Bell 1989, Schwarz et al., 1995; Harel and Futerman, 1993; Furuya et al., 1995), and transformation (Hakomori, 1981; Morton et al., 1994), and in tumor metastasis (Morton et al., 1994, Thurin et al., 1986, Cheresh et al., 1984). However, any role for glycosylceramides in the progression of multidrug resistance has not previously been noted, nor have any high levels of expression been noted in MDR cancers.

The inventors have shown, for the first time, the accumulation of glycosylceramide in cells expressing the MDR phenotype. These compounds were readily radiolabeled by preincubation of cells with sphingoglycolipid precursors, and their synthesis was found to be sensitive to sphingolipid biosynthesis inhibitors. The identified lipids contained a long-chain sphingoid base, fatty acids of either 16 (palmitic), or 24 carbons (nervonic, lignoceric) and a sugar moiety. The sugar moiety has been found mainly as glucose, but could be any other mono-, di- or complex saccharide. Palmitic, nervonic, and lignoceric are among the most common aliphatic species known to comprise sphingolipids (Vance and Vance, 1985). Additionally, the absence of α-hydroxy fatty acids (i.e., cerebronic) indicates that the sugar moiety of the glycosylceramides in MDR cells is glucose rather than galactose, since glucosylceramide contains little, if any, α-hydroxy fatty acid (Vance and Vance, 1985).

The enzyme responsible for glycolipid degradation in cells is glucosylcerebrosidase (Grabowski et al., 1990). Deficiencies in this enzyme result in marked accumulation of glucosylceramide, the major degradation product of complex glycosphingolipids (Grabowski et al., 1990, Nilsson and Svennerholm, 1982). Such is the situation expressed in fibroblasts from patients with Gaucher's disease (Grabowski et al., 1990, Nilsson and Svennerholm, 1982).

The accumulation of glycosylceramides in MDR cells may reflect a resistance mechanism, alone, or be part of a synergistic mechanism of cell survival. As such, P-gp activity, suggested to be dependent upon lipid environment (Al-Awqati, 1995; Shimabuku et al., 1992; Ruetz and Gros, 1994), may be regulated by glycosylceramides.

Cerebrosides

Cerebrosides have a single sugar linked to ceramide. Those with galactose are characteristically found in the plasma membranes of neural tissue, and those with glucose are found in the plasma membrane of non-neural tissues. About 25% of the brain cerebroside exists normally in the form of the corresponding 3'-sulfate esters; these cerebroside sulfates or sulfatides thus constitute about 6% of the total lipid of this neural tissue. The hydrophilicity of these derivatives is enhanced considerably by attachment of the formally charged, anionic group. A smaller fraction of the brain cerebrosides also bear an additional fatty acyl group, esterifying the terminal, primary hydroxyl group of the sugar moiety; these substances possess three long-chain hydrophobic groups and are unusual among biomembrane amphiphilic lipids in this respect.

With the exception of these last-named, quantitatively minor derivatives, the cerebrosides are bicaudal, and the single sugar moiety appears to have sufficient hydrophilicity to permit their serving as structural units of biomembranes. This indeed seems to be their principal function in myelin. Those that occur in the outer face of the cytoplasmic membranes, however, have a different, very important function, namely, as a site for glycosidic attachment of one or more of an assortment of hexose, N-acylated hexosamine, and sialic acid units, forming ceramide oligosaccharides with immunologic properties. These substances are firmly anchored in the cell membrane by the hydrophobic effect of the apolar groups of their ceramide moieties, but their oligosaccharide moieties extend into, and are thus readily accessible to, components of fluids bathing the cell. They are intimately involved in such phenomena as cell recognition and specific binding of bacterial toxins and protein hormones.

Gangliosides

The most complex of the glycolipids are the gangliosides, which contain one or more sialic acid residues (also known as N-acetylneuraminic acid, or NANA), which gives them a net negative charge. Gangliosides are most abundant in the plasma membrane of neurons, where they constitute about 6% of the total lipid mass, though they are found in smaller quantities in most cell types. So far, more than 30 different gangliosides have been identified. The ganglioside $G_{M1}$ acts as a cell-surface receptor for the bacterial toxin that causes the debilitating diarrhea of cholera. The toxin enters the cell and leads to a prolonged increase in the concentration of intracellular cyclic AMP, which in turn causes a large efflux of Na+ and water into the intestine. Although binding bacterial toxins cannot be the normal function of gangliosides, such observations suggest that these glycolipids may also serve as receptors for normal signaling between cells.

Methods of Detection

Chromatographic Methods of Detection

The present invention encompasses methods for the detection of multidrug resistance in cancer cells by determining the sphingoglycolipid content of cancer cells and comparing the level of certain sphingoglycolipids with those levels observed in normal cells of the same type. Generally, these methods will follow the methods described in the examples of the initial characterization of sphingolipid content.

Briefly, one will generally radiolabel the lipid components of a cell by incubation of the cell with [$^3$H]carbon-containing molecules that are direct or indirect precursors in lipid biosynthesis. Separation of labeled lipid components from (i) non-lipid components and (ii) each other will then permit quantitation of the different lipid species. Quantitation of separated components may be achieved by any standard methodology, but would include photodenistometric scanning of TLC plates or scintillation counting of membrane bound or liquid samples separated by various chromatographic techniques.

Any of a wide variety of chromatographic procedures may be employed. For example, Δ thin layer chromatography, gas chromatography, high performance liquid chromatography, paper chromatograph, affinity chromatograph or supercritical flow chromatography may be employed. See Freifelder, 1982.

Partition chromatography is based on the theory that if two phases are in contact with one another, and if one or both phases constitute a solute, the solute will distribute itself between the two phases. Usually, partition chromatography employs a column which is filled with a sorbent and a solvent. The solution containing the solute is layered on top of the column. The solvent is then passed through the column, continuously, which permits movement of the solute through the column material. The solute can then be collected based on is movement rate. The two most common types of partition chromatograph are paper chromatograph an d thin-layer chromatograph (TLC); together these are called adsorption chromatography. In both cases, the matrix contains a bound liquid. Other examples of partition chromatography as gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

Monoclonal Antibody Production and Methods of Detection Using Antibodies

Antibodies against sphingoglycolipids will be useful in the present invention. primarily in assays for the detection of sphingoglycolipids. Means for preparing and characterizing antibodies are well known in the art (see, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat.

Immunogenic composition of the invention include sphingoglycolipid derivatives or fragments and the like. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a compound to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and tittering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid. Radioimmunoassays, enzyme immunoassays, cytotoxicity assays, plaque assays, dot immunobinding assays, and the like, may be used.

Where one desires to generate an anti-sphingoglycolipid antibody with defined activity, one would generally screen the candidate hybridomas to identify those hybridomas that produce antibodies that have the desired inhibitory or stimulatory properties. Any selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Certain aspects of the present invention relates to the detection of glycosylceramides. One method of detecting glycosylceramides uses immunoassays for glycosylceramides. Antibodies and other toxin binding proteins (i e., cell surface receptors) that recognize a product or by-product of aglycosylceramides of the present invention are contemplated to be useful in the detection of glycosylceramides in the immunoassays.

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the anti-glycosylceramide- or glycosylceramide by product-specific antibodies of the invention are immobilized onto a selected surface exhibiting protein affinity, such as a well in a polystyrene microtiter plate. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen, followed by the addition of a third antibody that has binding affinity for the second antibody, with the third antibody being linked to a detectable label.

In another exemplary ELISA, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

Assays for sphingoglycolipids of the present invention also can determine normal/abnormal tissue distribution for diagnostic purposes. Methods for in vitro and in situ analysis are well known and involve assessing binding of antigen-specific antibodies to tissues, cells or cell extracts. These are conventional techniques well within the grasp of those skilled in the art. For example, the antibodies of the present invention may be used in conjunction with both fresh-frozen and formalin-fixed, paraffin-embedded tissue blocks prepared for study by immunohistochemistry (IHC). Each tissue block may consist of 50 mg of residual "pulverized" prostate tumor. The method of preparing tissue blocks from these particulate specimens has been successfully used in previous IHC studies of various prognostic factors, e.g., in breast cancer, and is well known to those of skill in the art. (Abbondanzo et al., 1990; Allred et al., 1990; Brown et al., 1990)

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

Assays for Additional Sphingoglycolipids Associated with MDR

In accordance with the present invention, there also are provided methods for the identification of additional sphingoglycolipids that correlated with multidrug resistance. This will be accomplished in essentially the same manner as the identification of the compounds identified herein.

Basically, one will screen drug insensitive cells for sphingoglycolipids that are present in amounts that differ from the amounts found in drug sensitive cells of the same type. Typically, the multidrug resistant cell will be cancer cells, such as lymphoma, melanoma, sarcoma, leukemia, retinoblastoma, hepatoma, myeloma, glioma, mesothelioma and carcinoma cells.

The method by which the lipid content of the cell is measured may comprise chromatographic separation of the components of said cell, and the chromatographic separation may comprise thin layer chromatography, gas chromatography, high performance liquid chromatography, paper chromatography, affinity chromatograph or supercritical flow chromatography. Preferred embodiments are described in the accompanying examples.

Once a lipid species has been identified as correlating with MDR, further analysis will be performed to determine the precise identity of the drug. A preferred diagnostic method is mass spectroscopy, although other methods may employed.

Inhibition of Sphingoglycolipid Synthesis and Chemosensitization

"Chemosensitizers", agents that increase the sensitivity of MDR cells to the toxic influence of previously less effective drugs, are intriguing in their mode of action (Tsuruo et al., 1981; Nayfield, 1995; Slater et al., 1986; Solary et al., 1991). The effect of different MDR chemosensitizers on sphingoglycolipid metabolism was studied, and subsequently the relationship between the observed inhibition of glycosylceramide synthesis and circumvention of MDR was analyzed.

Tamoxifen has been reported to reverse MDR via direct binding to P-glycoprotein (Callaghan and Higgins, 1995; Kirk et al., 1994). In the present study the inventors identified a new cellular target for tamoxifen, namely, sphingoglycolipid metabolism. Tamoxifen is shown here to drastically inhibit the synthesis of glycosylceramide and to suppress synthesis of higher gangliosides in MCF-7-AdrR cells.

Tamoxifen may be a general modulator of sphingoglycolipid synthesis, since a similar inhibitory effect was elicited by the drug in KB-V-1, a vinblastine-resistant epidermoid carcinoma. Similar inhibition by tamoxifen also was observed in three melanoma lines grown from human tumors. In addition, verapamil, and cyclosporin A, two well known MDR reversing agents, are also capable of inhibiting glycosylceramide synthesis, suggesting that this mechanism of action is a common denominator. A reduction in cell glycosylceramide content, as demonstrated in the present study, may define an important mechanism contributing to circumvention of MDR.

Inhibition of ceramide glycosylation is one of the key molecular mechanisms underlying tamoxifen influence of glycosylceramide metabolism. The inventor have shown that this inhibition was specific to sphingoglycolipid synthesis since sphingomyelin metabolism was not influenced by tamoxifen. Previous work has reported an inhibition of acid sphingomyelinase activity by tamoxifen and other MDR circumventors (Jafferezou et al., 1995); however, these studies did not indicate whether sphingomyelin levels were altered.

Further, the inventors have shown that synthesis of ceramide remained unchanged in the presence of tamoxifen, indicating that the tamoxifen site of action is distal to ceramide synthesis. Furthermore, the use of a cell-permeable short-chain analog of ceramide ($C_6$-ceramide) showed that glycosylation of $C_6$-ceramide to $C_6$-glycosylceramide clearly occurs in MCF-7-AdrR cells; however, glycosylation was drastically inhibited by tamoxifen. This, as well as inhibition of natural endogenous glycosylceramide synthesis by tamoxifen (FIG. 10, and FIG. 14B), strongly implies that tamoxifen inhibits UDP-glucose:ceramide glucosyltransferase activity.

In order to directly assess the MDR-reversal efficacy of tamoxifen, the sensitivity of MCF-7-AdrR cells to adriamycin insult in an in vitro growth inhibition assay was examined. This type of assay is used extensively as a hallmark of MDR circumvention and chemosensitivity (Kirk et al., 1994; Watanabe et al., 1995). Tamoxifen potently sensitized MCF-7-AdrR cells to adriamycin, while triphenylbutene was ineffective. The same results were obtained when assaying drug capacity to inhibit glycosylceramide synthesis, namely, tamoxifen strongly inhibited while triphenylbutene was a poor inhibitor. In addition, verapamil, and cyclosporin A, which reverse adriamycin-resistance in K562 cells (Watanabe et al., 1995), are shown here to inhibit glycosylceramide synthesis with similar effective concentrations (FIG. 11). These results clearly align the capacity of drugs to inhibit glycosylceramide synthesis with efficacy to circumvent MDR.

The use of PPMP, a specific inhibitor of UDP-glucose:ceramide glucosyl-transferase activity (Abe et al., 1995; Inokuchi et al., 1987; Rani et al., 1995; Schwarz et al., 1995), resulted in an inhibition glycosylceramide formation in the low micromolar range ($IC_{50}$ of 0.9 $\mu M$), a similar effective concentration reported in other studies (Rani et al., 1995; Schwarz et al., 1995). Intriguingly, PPMP, at a concentration shown to maximally inhibit glycosylceramide formation, while having no influence itself on cell viability, induced clear sensitization of MCF-7-AdrR cells to adriamycin. Although, at high concentrations (>30 $\mu M$), PPMP can act as a toxic lipophilic amine (Rosenwald and Pagano, 1994), the relatively low concentration used in this study, together with the observation that compound alone had little effect on MCF-7-AdrR cell survival, indicate that PPMP restores cell sensitivity to adriamycin.

Although acquiring and maintaining the MDR phenotype involves multiple cellular adjustments, it now appears that there in an important role for sphingoglycolipids in this process. Drug resistance continues to be a major obstacle to successful chemotherapy. Advances in the molecular principles of drug resistance will supply viable tools for combating obstacles to drug treatment. Tamoxifen has long been viewed with curiosity regarding estrogen receptor-independent actions (Kellen, 1996), particularly with respect to reversal of MDR (Fan et al., 1994) and synergy in combination chemotherapy (McClay and McClay, 1994).

Therefore, it is an goal of the present invention to provide methods of inhibiting the formation of sphingoglycolipids in MDR cancer cells. In its most basic form, this involves subjecting the cancer cells to an effective concentration of an inhibitor of sphingoglycolipid formation, such as one of the family of compounds discussed above, or with a candidate substance identified in accordance with the candidate screening assay embodiments, as described below. It is believed that, by inhibiting the sphingoglycolipid formation of such cells, one will be able to treat various aspects multidrug resistant cancers by, in effect, resensitizing these cells to chemotherapeutic agents. The use of such inhibitors of sphingoglycolipid formation to block, for example, glycosylceramide formation, will serve this purpose.

The particular routes and doses of agents will vary depending on the clinical situation, and such determinations must be left to the clinician. The various parameters to be considered include the age, weight, sex and overall state of health of the patient, the type, size and location of the tumor, the ability of the patient to tolerate the toxicity of the drug, and a host of other factors.

MDR Reversing Agents

A variety of different agents that reverse MDR may be used according to the present invention. As discussed above and in the Examples below, the antihormone tamoxifen surprisingly has been shown to inhibit the formation of certain sphingoglycolipids. Various hormones and antihormones have been shown to reverse MDR, and some bind directly to P-glycoprotein. Besides tamoxifen, progesterone, toremifene and ICI 164384 and MK-329 also have anti-MDR activity. The recommended dose for tamoxigen is 20 to 40 mg daily, administered orally in two doses.

Calmodulin is an intracellular calcium-binding protein that plays an important role in a variety of cellular activities. The calcium-sequestrating role of calmodulin prompted efforts to look at the MDR-reversing effects of the potent calmodulin antagonist trifluoperazine and many similar antipsychotic phenothiazines were found to have similar MDR-reversing activities in experimental systems. Other candidate drugs are thioridzaine, chlorpromazine, prochlorperazine, perphanazine, clomipramine, fluphenazine, clopenthixol, trifluopromazine, flupentixol, flunarazine, nifedipine, nimodipene, nitrendipine, nicardipene and chlorprothixene.

A number of antibiotics now have been found to reverse experimental MDR phenotypes, including cephalosporins, erythromycin, monensin and a variety of vinca alkaloid derivatives. Of particular interest is the anticancer agent thaliblastine, which binds to P-glycoprotein and reverses adriamycin resistance of P388 MDR cells.

Indole aklyoids such as the antimalarial quinine and structurally related compounds have been found to have MDR-reversing activity. Many of these compounds are neurohumoral antagonists that include reserpine and yohimbine. Other compounds include chloroquine, catharanthine, quinacrine and quinolones.

Cyclosporins and cyclosporin analogs are some of the most effect MDR-reversing agents available. Although these drugs have a high affinity for P-glycoprotein, the reversal effects do not correlate consistently with either drug accumulation or direct interaction with P-glycoprotein. Included in this group are cyclosporin A, SDZ-280-446, B3-243, FK-506 and patellamide D.

Pharmaceutical emulsifying agents have recently been shown to have MDR-reversing activity. Non-toxic amounts of several have been demonstrated to compete for P-glycoprotein binding with photoaffinity azidopine. Such compounds include Cremophor EL, Solutol HS15, Triton X-100, Thesit and Tween 80.

Various other chemicals have been shown to exhibit MDR-reversing properties, including amilorides, transferrin, forskolin, amiodarone, benziquinamide, trazadone, dipyramidole, droloxifene, raloxifene, ICI 164, 384 (and related "Zeneca" estrogen analogs), toremifene, keoxifene, trioxifene, clomiphere, 4-hydroxy tamoxifen, nafoxidene, kaempferol, PPMP, LY 335979 (Syntex), verapamil and verapamil analogs, staurosporine, CGP 41251, RO 31-8220, quercetin, taxol, valinomycin, nonactin, benzofuranylethanolamines, propafenone, VX-710 (Vertex) keoconazole, itraconazole and the triazine, S 9788.

Assays for Additional Inhibitors of Sphingoglycolipid Formation for Use in the Invention In certain embodiments, the present invention concerns a method for identifing further sphingoglycolipid inhibitors. It is contemplated that this screening technique will prove useful in the general identification of any compound that will inhibit sphingoglycolipid production in MDR cancer cells.

Useful compounds in this regard will not be limited to those mentioned above. The active compounds may include fragments or parts of naturally-occurring compounds or may be only found as active combinations of known compounds which are otherwise inactive. However, prior to testing of such compounds in humans or animal models, it may be necessary to test a variety of candidates to determine which have potential.

Accordingly, in screening assays to identify pharmaceutical agents which inhibit sphingoglycolipid formation in MDR cancer cells, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

In these embodiments, the present invention is directed to a method for determining the ability of a candidate substance to inhibit the synthesis of sphingoglycolipid content of multidrug resistant cancer cells and to concomitantly sensitize the cells to other chemotherapeutic agents, the method including generally the steps of (a) obtaining an MDR cancer cell; (b) admixing a candidate substance with the MDR cell; and (c) determining the ability of the candidate substance to inhibit the sphingoglycolipid content of the MDR cancer cell.

To identify a candidate substance as being capable of inhibiting sphingoglycolipid formation, one would measure or determine the sphingoglycolipid composition of a cell that expresses sphingoglycolipids, preferably a MDR cancer cell, in the absence of the added candidate substance. One would then add the candidate substance to the cell and re-determine the sphingoglycolipid composition in the presence of the candidate substance. A candidate substance which reduces the sphingoglycolipid composition relative to the composition in its absence is indicative of a candidate substance with inhibitor capability.

The candidate screening assay is quite simple to set up and perform, and is related in many ways to the assay discussed above for determining glycosylceramide content Thus, after obtaining an suitable test cell, one will admix a candidate substance with the cell, under conditions which would allow the formation of sphingoglycolipid formation, for example, glycosylceramide inhibition.

"Effective amounts", in certain circumstances, are those amounts effective at reproducibly reducing sphingoglycolipid formation in MDR cancer cells in comparison to their normal levels. Compounds that achieve significant appropriate changes in activity will be used. If desired, a battery of compounds may be screened in vitro to identify other agents for use in the present invention.

A significant decrease in sphingoglycolipid formation, e.g., as measured using chromatography techniques (quantitation by densitometry or liquid scintillation spectroscopy), are represented by a reduction in glycosylceramide levels of at least about 30%–40%, and most preferably, by decreases of at least about 50%, with higher values of course being possible. Chromatography assays that measure glycosylceramide contents and enzyme assays that measure glycosylceramide formation are well known in the art and may be conducted in vitro or in vivo.

Alternatively, it may be desirable simply to measure inhibition of growth of cancer cells, for example, by measuring growth according to the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Assays may be conducted as described by Mosmann et al., 1983; Rubinstein et al., 1990 (incorporated herein by reference). Therefore, if a candidate substance exhibited inhibition in this type of study, it would likely be a suitable compound for use in the present invention.

Quantitative in vitro testing of the inhibitor is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context, for example, as disclosed herein. There is considerable information available on the use and doses of chemotherapeutic agents alone, which information may now be employed with the present invention. The skilled artisan is referred to "Remington's Pharmaceutical Sciences" 15th Edition (incorporated herein by reference) for guidance on types of chemotherapeutic agents that may be used in the present invention.

Additional Chemotherapeutic Agents for Combination Treatments

A wide variety of chemotherapeutic agents may be used in combination with the inhibitors of glycosylceramide formation of the present invention. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

Doxorubicin

Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 $mg/m^2$, 150 $mg/m^2$, 175 $mg/m^2$, 200 $mg/m^2$, 225 $mg/m^2$, 250 $mg/m^2$, 275 $mg/m^2$, 300 $mg/m^2$, 350 $mg/m^2$, 400 $mg/^2$, 425 $mg/m^2$, 450 $mg/m^2$, 475 $mg/m^2$, 500 $mg/m^2$. Of course, all of these dosages are exemplary, and any dosage in-between these points is also expected to be of use in the invention.

In certain aspects of the present invention the inventors have used inhibitors of glycosylceramide formation in combination with adriamycin to enhance the chemotherapeutic effects of adriamycin in cells resistant to adriamycin.

Bleomycin

Bleomycin is a mixture of cytotoxic glycopeptide antibiotics isolated from a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted. Bleomycin may be given by the intramuscular, intravenous, or subcutaneous routes.

Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 $mg/m^2$ for 5 days every three weeks for a total of three courses. Exemplary doses may be 0.50 $mg/m^2$, 1.0 $mg/m^2$, 1.50 $mg/m^2$, 1.75 $mg/m^2$, 2.0 $mg/m^2$, 3.0 $mg/m^2$, 4.0 $mg/m^2$, 5.0 $mg/m^2$, 10 $mg/m^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

VP16

VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 $mg/m^2$ or as little as 2 $mg/m^2$, routinely 35 $mg/m^2$, daily for 4 days, to 50 $mg/m^2$, daily for 5 days have also been used. When given orally, the dose should be doubled. Hence the doses for small cell lung carcinoma may be as high as 200–250 $mg/m^2$. The intravenous dose for testicular cancer (in combination therapy) is 50 to 100 $mg/m^2$ daily for 5 days, or 100 $mg/m^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor

Tumor Necrosis Factor [TNF; Cachectin] is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

Taxol

Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 $mg/m^2$ per day for 5 days or 210 to 250 $mg/m^2$ given once every 3 weeks. Of course, all of these dosages are exemplary, and any dosage in-between these points is also expected to be of use in the invention.

Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

Vinblastine

When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

Carmustine

Carmustine (sterile carmustine) is one of the nitrosoureas used in the treatment of certain neoplastic diseases. It is 1,3bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medulloblaysoma, astrocytoma, ependymoma, and metastatic brain tumors. Also it has been used in combination with prednisone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m² intravenously every 6 weeks. This may be given as a single dose or divided into daily injections such as 75 to 100 mg/m² on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m², 20 mg/m², 30 mg/m², 40 mg/m², 50 mg/m², 60 mg/m², 70 mg/m², 80 mg/m², 90 mg/m², 100 mg/m². The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject.

Melphalan

Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a $pKa_1$ of ~2.1. Melphalan is available in tablet form for oral administration and has been used to treat multiple myeloma.

Available evidence suggests that about one third to one half of the patients with multiple myeloma show a favorable response to oral administration of the drug. Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject Cyclophosphamide Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH₂CH₂)₂N—POCl₂] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day . A dose 250 mg/kg/day may be administered as an antineoplastic. Because of gastrointestinal adverse effects, the intravenous route is preferred for loading. During maintenance, a leukocyte count of 3000 to 4000/mm³ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil

Chlorambucil (also known as leukeran) was first synthesized by Everett et al. (1953). It is a bifunctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m²/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan 1Busulfan (also known as myleran) is a bifunctional alkylating agent. Busulfan is known chemically as 1,4-butanediol dimethanesulfonate, but is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours. The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these figures as determined by the clinician to be necessary for the individual being treated.

Pharmaceutical Compositions and Routes of Administration

Aqueous compositions of the present invention will have an effective amount of an inhibitor of sphinglycolipid formation, alone or in combination with an effective amount of a compound (chemotherapeutic agent) that is a chemotherapeutic agent as exemplified above. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains glycosylceramide synthesis inhibitory compounds alone or in combination with a chemotherapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Kits

All the essential materials and reagents required for determining sphingoglycolipid levels in a sample or for inhibiting tumor cell proliferation may be assembled together in a kit. When the components of the kit are provided in one or more liquid solutions, the liquid solution preferably is an aqueous solution, with a sterile aqueous solution being particularly preferred.

For the detection of sphingoglycolipids, the kit may contain materials for chromatographic separation, such as columns, beads, resins, gel matrices, filters, TLC plate, buffers and appropriate solvents. Alternatively, if the detection is via immunologic means, the kit may contain antibodies directed to the sphingoglycolipids, secondary antibodies that binding primary antibodies, labels or signal generating compounds (either conjugated or unconjugated) and various reagents for the generation and detection of signals.

For in vivo use, an inhibitor of sphingoglycolipid formation, alone or in combination with, a chemotherapeutic agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the sphingoglycolipid formation inhibitor and/or the chemotherapeutic drug, or explaining the assays for determining sphingoglycolipid levels in samples.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Experimental Procedures

Materials

Sphingosine, sphingomyelin, and ceramides were purchased from Avanti Polar Lipids (Alabaster, Ala.). PPMP was from Biomol (Plymouth Meeting, Pa.). L-Cycloserine, $FB_1$, and PPMP were from Biomol (Plymouth Meeting, Pa.). Glucocerebroside (Gaucher's spleen) standard was from Matreya, Inc. (Pleasant Gap, Pa.). EN$^3$HANCE, [$^3$H]L-serine (21.7 Ci/mmol), [9,10-$^3$H]palmitic acid (56.5 Ci/mmol), and D-[6-$^3$H(N)]-galactose (29.5 Ci/mmol) were purchased from DuPont/New England Nuclear. Liquid scintillation cocktail (EcoLume) was from ICN Biomedicals. Silica Gel G thin-layer chromatography plates were from Analtech (Newark, Del.). Solvents were from Fisher Scientific. RPMI-1640 Media (Cellgro™) was purchased from Mediatech (Hemdon, Va.), fetal bovine serum (FBS) was from HyClone (Logan, Utah), and corning cultureware was from Corning-Costar. All other biochemicals were from Sigma.

Cell Culture

MCF-7-wt and MCF-7-AdrR (adriamycin-resistant) cells were provided by the National Cancer Institute. Cells were maintained in RPMI-1640 medium containing 10% FBS (v/v), 50 units/ml of penicillin, 50 µg/ml of streptomycin, and L-glutamine (584 mg/L).

KB-3-1 human oral epidermoid carcinoma cells (parent, drug-sensitive) and KB-V-1 cells (highly multidrug resistant subclone) were provided by the National Cancer Institute. Cells were grown in high glucose (4.5 gm/L) Dulbecco's modified Eagle's medium containing 10% FBS and other components described above. The KB-V-1 cell was maintained with vinblastine (1.0 µg/ml) in the medium.

NIH:OVCAR-3 cells (human ovarian adenocarcinoma, drug-resistant) were obtained from the American Type Culture Collection and grown in RPMI-1640 medium containing insulin (10 µg/ml), 10% FBS and other components listed above.

All cells were cultured in a humidified, 6.5% $CO_2$ atmosphere, tissue culture incubator, and subcultured once a week, using 0.05% trypsin and 0.53 mM EDTA solution, to maintain logarithmic growth.

Lipid Mass Analysis—Cell lipids were analyzed by TLC separation and charring of the chromatogram. Briefly, total cellular lipids were extracted by the method of Bligh and Dyer (1959), and equal aliquots (by weight) from each sample were spotted on TLC plates. The plates were developed using solvent system I or II (see below), air-dried for 1 h and sprayed using a 35% solution of sulfuric acid in water. The lipids were charred by heating in an oven at 180° C. for 30 min, and resulting black bands were visualized and photographed. Bands can be further quantitated by photodensitometric scanning.

Cell Radiolabeling and Analysis of Sphingolipids

MCF-7 cells, grown in medium containing 10% FBS, were switched to media containing 5% FBS. Cell lipids were radiolabeled by adding [$^3$H]serine (2.0 $\mu$Ci/ml), [$^3$H] palmitic acid (1.0 $\mu$Ci/ml), or [$^3$H]galactose (1.0 $\mu$Ci/ml) to the culture medium for the indicated times. Other radiolabels can be substituted. Cells were then rinsed twice with PBS, pH 7.4, and 2 ml of ice-cold methanol containing 2% acetic acid was added. The cells were scraped free, transferred to glass test tubes (13×100 mm), and lipids were extracted by the addition of chloroform (2 ml) followed by water (2 ml). The resulting organic lower phase was withdrawn and evaporated under a stream of nitrogen. Lipids were resuspended in 100 $\mu$L of chloroform/methanol (1:1, v/v), and aliquots were applied to TLC plates. Lipids may be estimated by the method of Bligh and Dyer (1959), or any other similar method known to those of skill in the art.

When using [$^3$H]galactose, radiolabeled cells were transferred to glass tubes with PBS (1 ml), glucocerebroside (2.5 $\mu$g) was added to aid recovery, and lipids were extracted consecutively three times with 2 ml of chloroform/methanol (1:1, v/v).

Lipid analysis was carried out by TLC using solvent system I: chloroform/methanol/ammonium hydroxide (40:10:1, v/v) for glycosylceramide separation, solvent system II: chloroform/methanol/water (60:40:8, v/v) for sphingoglycolipid separation, or solvent system III: chloroform/methanol/acetic acid/water (50:30:7:3, v/v) for sphingomyelin separation. For determination of ceramides, an aliquot of the chloroform-soluble lipids was base-hydrolyzed in 0.1N KOH in methanol for 1 h at 37° C., lipids were re-extracted, and separated by TLC using solvent system IV: hexane/diethyl ether/formic acid (60:40:1, v/v).

Radiochromatograms were sprayed with EN$^3$HANCE, and exposed for 3–7 days for autofluorgraphy. TLC areas, aligned with bands on the autoradiographs or with iodine-stained commercial lipid standards, were scraped from the plate. Water (0.5 ml) was added to the plate scrapings followed by 4.5 ml of EcoLume counting fluid, and the samples were quantitated by liquid scintillation spectrometry.

Purification of Glycosylceramides Lipid-1 and -2

The compounds in question, extracted with total lipids from MCF-7-AdrR cells, were resolved from other lipids on preparative TLC using Silica Gel H plates developed in solvent system II. The appropriate region of the TLC plate was then scraped into test tubes and lipids 1 and 2 were extracted with chloroform/methanol/acetic acid/water (50:25:1:2, v/v). The samples were centrifuged, and the solvent was transferred to new glass tubes and evaporated to dryness under nitrogen.

Fast-Atom Bombardment Mass Spectrometry of TLC-isolated Lipids 1 and 2

FAB/MS spectra were acquired using a VG 70 SEQ tandem hybrid instrument of EBqQ geometry (VG analytical, Altrincham, UK). The instrument was equipped with a standard unheated VG FAB ion source and a standard saddle-field gun (Ion Tech Ltd., Middlesex, UK) that produced a beam of xenon atoms at 8 KeV and 1 mA. The mass spectrometer was adjusted to a resolving power of 1000 and spectra were obtained at 8 kV and at a scan speed of 10 sec/decade. 2-Hydroxyethyl disulfide was used as matrix in the negative FAB/MS, and triethanolamine was used as a matrix in the negative FAB/MS. Negative-FAB and positive-FAB give different values for the same compounds, due to charge (proton content) differences.

Cytotoxicity Assay

Cells were seeded in 96-well plates (2000 cells/well), in 0.1 ml RPMI 1640 medium containing 5% FBS, and incubated at 37° for 24 h before drug addition. Drug was added in medium (0.1 ml), and the cells were incubated at 37° for an additional 4 days. Vehicle (acetone, ethanol) was always added to control (minus drug) wells. The cytotoxic activity of a drug was determined using the Promega CellTiter 96™ AQ$_{ueous}$ MTS cell proliferation assay kit. Each experimental point was performed in six replicates. MTS/PMS solution (20 $\mu$l/well) was aliquoted into all wells, and the cells were incubated for 2–3 h, or until an O.D. of 0.9–1.0 was obtained as a highest reading. Thereafter, absorbence at 490 nm was recorded using an ELISA plate reader (Molecular Devices, San Diego, Calif.).

Example II

Radiolabelling Using Sphingolipid Precursors

Figure 2:
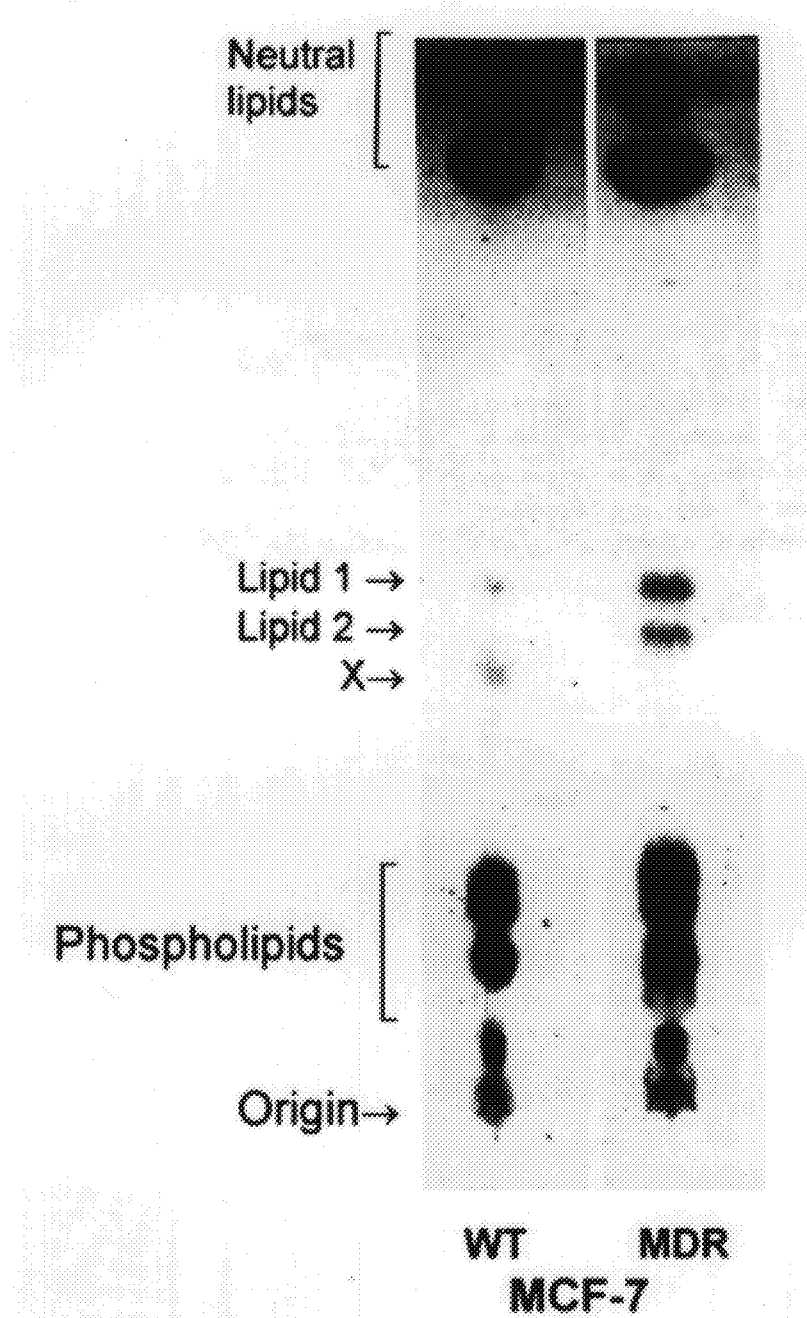
FIG. 2. Thin-layer chromatographic char of lipids from MCF-7-wt and MCF-7-AdrR cells. Extracted lipids, 100 μg/lane, were resolved using solvent system II. Lipids were visualized by $H_2SO_4$ charring as described in Example I, and identified by migration with commercial standards. X, unknown lipid.

During TLC analysis of total lipids obtained from drug-sensitive and drug-resistant cancer cells, we noted the presence of two compounds, migrating as a doublet, in drug-resistant cells. FIG. 2 shows the lipid composition of MCF-7-wt and MCF-7-AdrR cells. The compounds in question, marked lipid-1 and -2, migrated on TLC, in solvent system II, with R$f$ values of 0.5, and 0.45, respectively.

There was a remarkable difference in the appearance of the lipids in wt and MDR cells, the drug-sensitive cells being nearly devoid of lipid-1 and completely devoid of lipid-2. The chromatogram also shows that MCF-7-wt cells contain a lipid (lipid X) migrating just below lipid-2 (R$f$ value of 0.42). Preliminary work indicated that lipid-1 and -2 did not contain glycerol, choline, or ethanolamine, and migrated just bellow sphinganine (solvent system I). The sphingoid base nature of lipid-1 and -2 was further pursued.

Figure 6A:
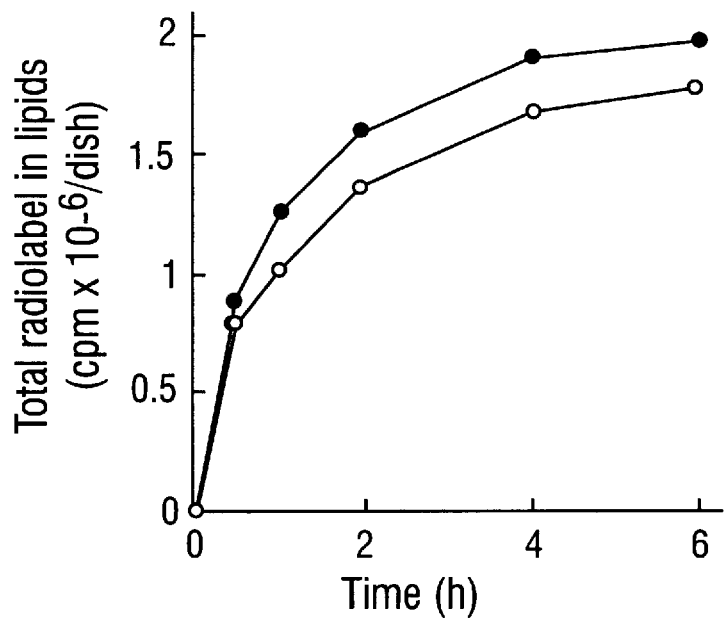
FIG. 6A, FIG. 6B and FIG. 6C. Time-course of [$^3$H] palmitic acid incorporation into total lipid, ceramide, and glycosylceramide in MCF-7-wt and MCF-7-AdrR cells. MCF-7-wt (○) and MCF-7-AdrR (●) cells (60×15 mm dishes) were incubated with 1.0 $\mu$Ci/ml [$^3$H]palmitic acid in RPMI-1640 medium containing 5% FBS. At the times indicated, lipids were extracted as described in Example I. Aliquots of the labeling medium were counted directly by liquid scintillation spectrometry to determine [$^3$H]palmitic acid uptake and incorporation (FIG. 6A). For ceramide detection, lipids were based-hydrolyzed as described in Example I and separated by TLC using solvent system IV (FIG. 6B). Glycosylceramides (lipid-1 and -2) were separated by TLC using solvent system II (FIG. 6C). After TLC resolution, quantitation of radiolabel in the relevant regions of the TLC plate was conducted as detailed in Example I. Results are from one of three experiments that gave similar results (FIG. 6A, FIG. 6C), and from the mean±SEM of duplicate samples of four separate experiments (FIG. 6B).
Figure 6B:
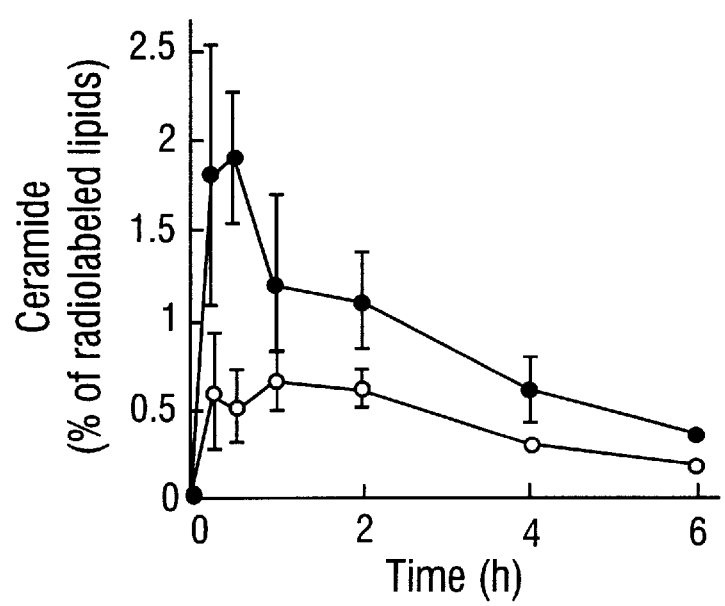

The possibility of accelerated glycosphingolipid synthesis was addressed by adding exogenous precursor to cultured cells. Indeed, sphinganine caused accelerated synthesis of glycosylceramide in MCF-7-AdrR but not in MCF-7-wt cells. Additionally, MCF-7-AdrR cells synthesized more ceramide during short-term incubation periods, compared to MCF-7-wt cells (FIG. 6B).

Thus, it is possible that MCF-7-AdrR cells modify ceramide synthase to be more active. This may be part of acquired biochemical changes occurring during acquisition of drug resistance resulting from continuous exposure to adriamycin. In line with our observations on ceramide metabolism in MCF-7 cells, sensitive or resistant to antineoplastic anthracyclines, is recent work by Bose et. al., showing that daunorubicin stimulates ceramide elevation in P388 and U937 cells, via activation of ceramide synthase (Bose et al., 1995). This supports the notion that a more active glycosphingolipid synthetic pathway exists in MDR cells.

On the other hand, our long-term experiments with radiolabeled precursors revealed that ceramide labeling was similar in MCF-7-wt and MCF-7-AdrR cells, whereas [$^3$H] glycosylceramide levels remained 8 to 10-fold higher (FIG. 6). These results may suggest that the short-term (30 min) changes in labeled ceramide reflect an enhanced radiospecific activity rather than changes in ceramide mass. The mass differences in glycosylceramide between the two cells was easily seen on TLC chars (FIG. 2). Thus, the accumulation of glycosylceramides in MCF-7-AdrR cells may also be explained by poor glycolipid degradation mechanisms.

MCF-7-wt and MCF-7-AdrR cells were incubated for 24 h in medium containing either [$^3$H]serine, [$^3$H]palmitic acid, or [$^3$H]galactose. The incorporation of radioactivity into cell lipids was assessed by autoradiography (FIG. 3) and by liquid scintillation counting of tritium in the indicated areas of the chromatogram. [$^3$H]Serine was incorporated into lipids of both MCF-7-wt and MCF-7-AdrR cells and was mainly confined to PE (43.7 and 29.5%, respectively), and SM (6.9 and 10.9%, respectively). However, the incorporation of [$^3$H]serine into lipid-1 and -2 was visible only in MCF-7-AdrR cells (FIG. 3A), where it accounted for 4.5% of total radiolabeled lipids compared to 0.52% in MCF-7-wt cells.

[$^3$H]Palmitic acid was likewise used for the synthesis of complex lipids in both wt and MDR cells, and was incorporated mainly to PC (35.9 and 41.1%, respectively), PE (9.4 and 9.5%, respectively), and SM (3.4 and 6.9%, respectively). However, biosynthesis of lipid-1 and -2 from palmitic acid precursor was much more marked in MDR cells (FIG. 3B).

Figures 3A, 3B, 3C:
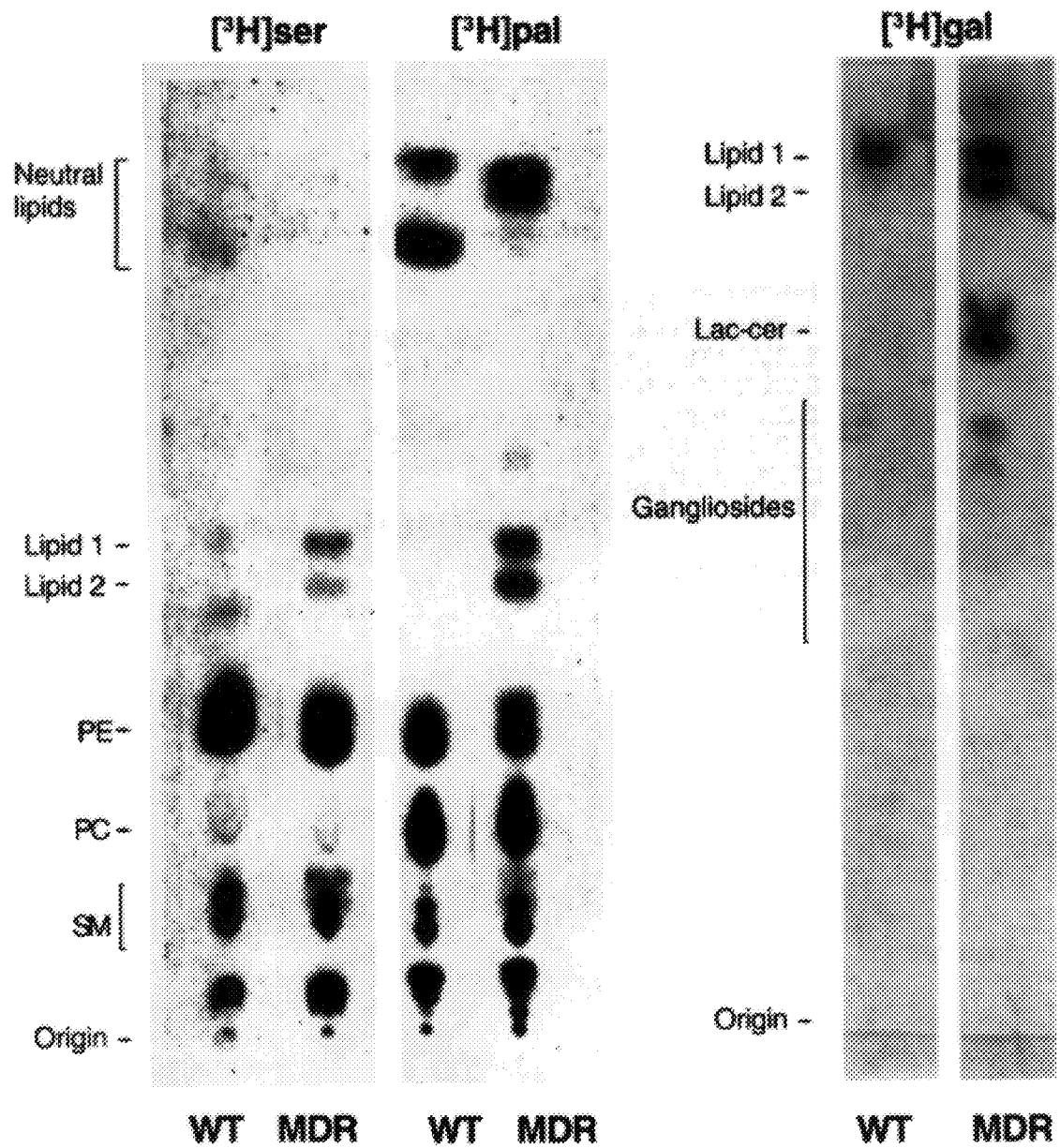
FIG. 3A, FIG. 3B and FIG. 3C. Autoradiograph of lipids from MCF-7 cells incubated with radiolabeled sphingolipid precursors. MCF-7-wt and MCF-7-AdrR cells (MDR), grown to near-confluency in 100×20 mm culture dishes, were labeled with [$^3$H]serine (FIG. 3A), [$^3$H]palmitic acid (FIG. 3B), or [$^3$H]galactose (FIG. 3C) for 24 h in RPMI- 1640 medium containing 0.1% BSA. Equal aliquots (based on uptake of radioactivity) of extracted cell lipids were analyzed by TLC using solvent system I (Panels A, B), and solvent system III (Panel C). The autoradiography of a representative chromatogram is shown. Abbreviations used: Lac-cer, lactosylceramide; SM, sphingomyelin; PC, phosphatidylcholine; PE, phosphatidylethanolamine.

The autoradiography in FIG. 3B, also shows that MCF-7-wt cells incorporate radioactivity into a lipid seen in the neutral lipid area. Indicated by its comigration with oleoyl alcohol (solvent system IV), this lipid is a fatty alcohol. This is in accordance with previous work showing that fatty alcohol accumulates in MCF-7 wt cells, but not in MDR MCF-7 variants (Welsh et al., 1994).

Qualitative data were obtained from experiments using [$^3$H]galactose. FIG. 3C, shows that [$^3$H]galactose was utilized by MDR cells for synthesis of lipid-1 and -2. Radio-incorporation was markedly pronounced in MDR cells, while MCF-7-wt demonstrated slight incorporation into lipid-1 and no incorporation into lipid-2. The all-inclusive data (FIG. 3) suggest that lipids 1 and 2, accumulating in MDR cells, are glycosphingolipids. Using various solvent systems for TLC separation, the migration of commercial glucocerebroside (Gaucher's spleen) was compared with lipid-1 and -2 radioactivity and found that the compounds comigrated.

Data thus indicate that lipids 1 and 2 are cerebrosides of the glycosylceramide type. Work in other cell types has amply demonstrated the central position played by glycosylceramide in glycolipid synthesis (Schwarz et al., 1995; Lee et al., 1985, Rani et al., 1995). Along these lines, FIG. 3C, shows other anticancer in MDR cells, although less pronounced, which comigrated with lactosylceramide and ganglioside standards.

Figure 4:
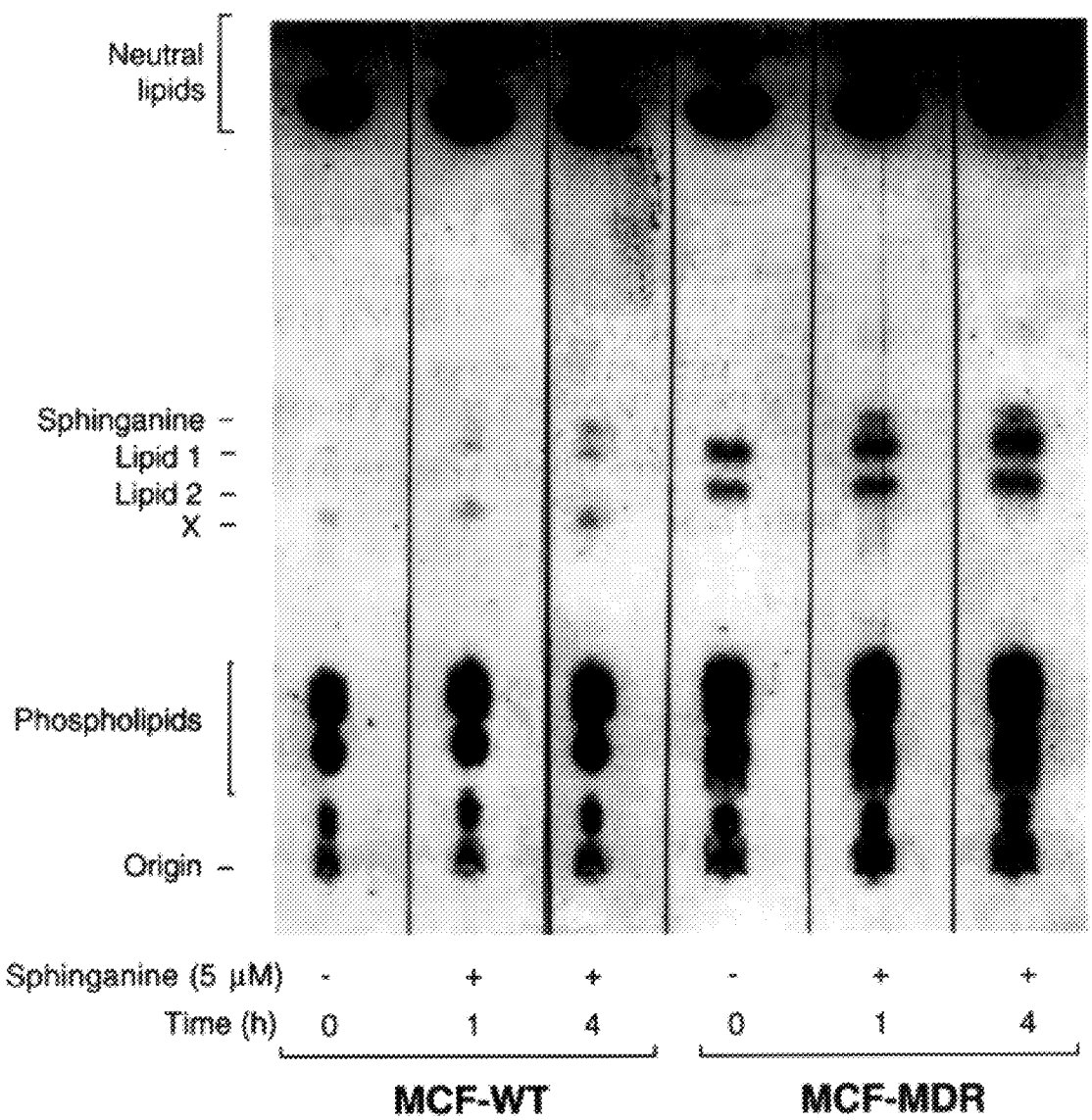
FIG. 4. Metabolism of sphinganine by MCF-7-wt and MCF-7-AdrR cells. Cells, in 100×20 mm culture dishes, were incubated with 5.0 $\mu$M sphinganine:BSA (prepared at a 1:1 molar ratio) for the times indicated. Lipids were extracted, a 100 $\mu$g lipid aliquot of each sample was resolved by TLC in solvent system II, and the TLC was charred as described in Example I. The data shown are representative of two independent experiments which gave similar results.

In order to verify that lipid-1 and -2 synthesis originates from a pathway involving sphingoid bases, sphinganine was added exogenously to the cell culture medium. As shown in FIG. 4, sphinganine supplement caused a time-dependent elevation in the mass of lipid-1 and -2 in MCF-7-wt and MCF-7-AdrR cells (detected by TLC charring); although, mass increases in MDR cells were strikingly more pronounced. In addition, whereas lipid-1 from both cells migrated with a like $R_f$ value of 0.53, lipid-2 did not appear in the MCF-7-wt cells in response to sphinganine supplementation. In its stead, synthesis of lipid X increased, indicating that lipid X is a sphingolipid.

Example III

Figure 1B:
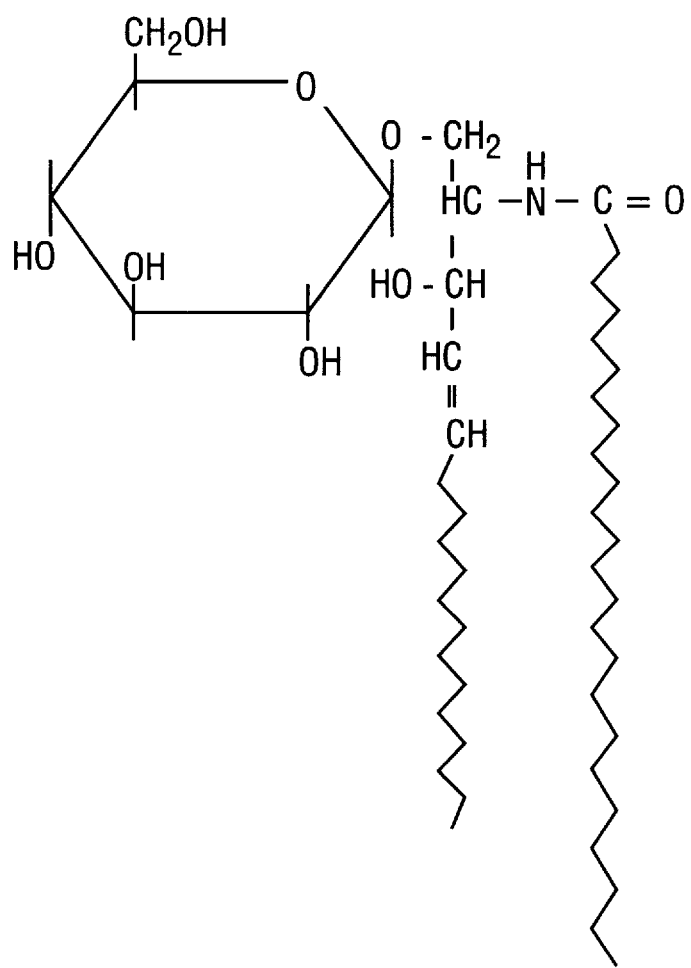

Effect of Inhibitors of Sphingolipid Biosynthesis on Lipid 1 and Lipid 2 Formation The effects of various inhibitors of sphingolipid biosynthesis were investigated, using MCF-7-AdrR cells, labeled with either [$^3$H]palmitic acid, or [$^3$H]serine. The first enzymatic reaction in sphingoid base biosynthesis, catalyzed by serine:palmitoyltransferase, is the formation of 3-ketosphinganine from serine and palmitoyl-CoA (FIG. 1).

Figures 5A, 5B, 5C:
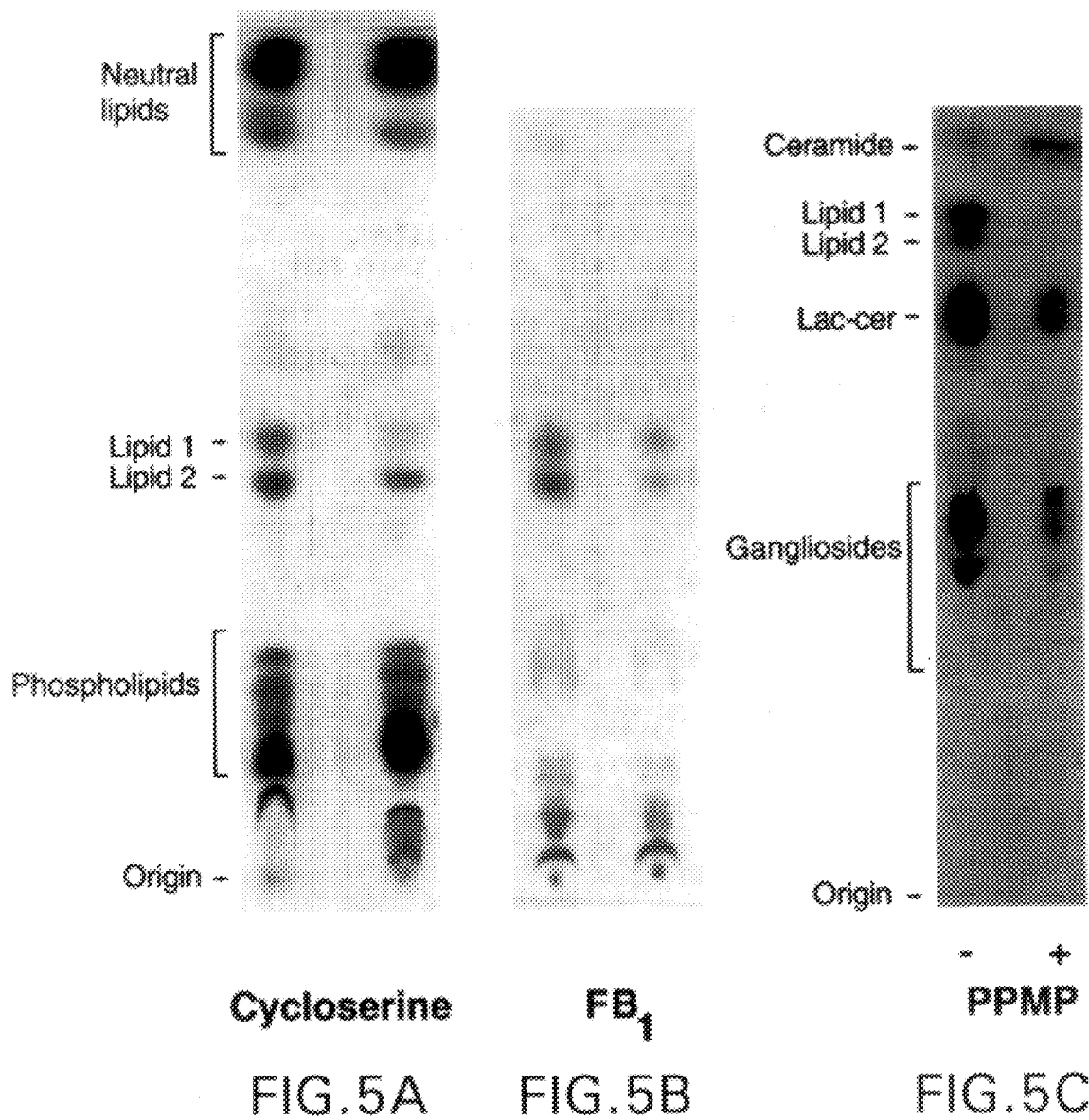
FIG. 5A, FIG. 5B, and FIG. 5C. Effect of inhibitors of sphingolipid biosynthesis on lipid-1 and -2 formation in MCF-7-AdrR cells. Cells, grown to near-confluency in 100×20 mm culture dishes, were radiolabeled with [$^3$H] palmitic acid (FIG. 5A), or [$^3$H]serine (FIG. 5B, FIG. 5C), in the presence or absence of 10 mM L-cycloserine (FIG. 5A), 50 $\mu$M FB$_1$ (FIG. 5B), or 20 $\mu$M PPMP (FIG. 5C), for 24 h in RPMI-1640 medium containing 0.1% BSA. Extracted lipids were analyzed by TLC using solvent system II (FIG. 5A, FIG. 5B), or solvent system III (FIG. 5C) as described in Example I. Lac-cer, lactosylceramide.

Preincubation of cells with L-cycloserine, an inhibitor of serine palmitoyl-CoA condensation, caused almost complete disappearance of lipid-1 and major inhibition of lipid-2 formation (FIG. 5A). Ceramide synthase, which catalyzes formation of ceramide via an acylation reaction, can be inhibited by $FB_1$ (Schwarz et al., 1995, Wang et al., 1991; Wu et al., 1995). Preincubation of MCF-7-AdrR cells with $FB_1$ caused a profound reduction in the level of both lipid-1 and -2 (FIG. 5B). In further experiments, the glycolipid nature of the accumulating lipids in MDR cells was investigated using PPMP, a specific inhibitor of β-glycosyltransferase (Schwarz et al., 1995, Lee et al., 1985, Rani et al., 1995). As shown in FIG. 5C, PPMP blocked completely the formation of lipid-1 and -2. This effect was accompanied by an elevation in ceramide levels. A concomitant reduction in lactosyceramide and gangliosides also occurred (FIG. 5C), reflecting the ability of PPMP to block glycolipid synthesis distal to glycosylceramide. These observations show that the metabolic steps governing the accumulation of lipid-1 and -2 are closely associated with glycosylation/deglycosylation events.

Example IV

Time Course for the Formation of Lipid-1 and Lipid-2

[$^3$H]Palmitic acid was used to determine the time course of lipid-1 and -2 formation, as well as that of ceramide. As shown in FIG. 6A, uptake and incorporation of [$^3$H]palnitic acid was nearly equal in MCF-7-wt and MCF-7-AdrR cells. FIG. 6B, shows that [$^3$H]palmitic acid was rapidly incorporated into ceramide, with 3.6-fold higher levels at 30 min in MCF-7-AdrR cells compared to MCF-7-wt cells. Thereafter (1–6 h), the levels of [$^3$H]ceramide decreased similarly in both cells, reflecting conversion of ceramide to sphingolipids.

Figure 6C:
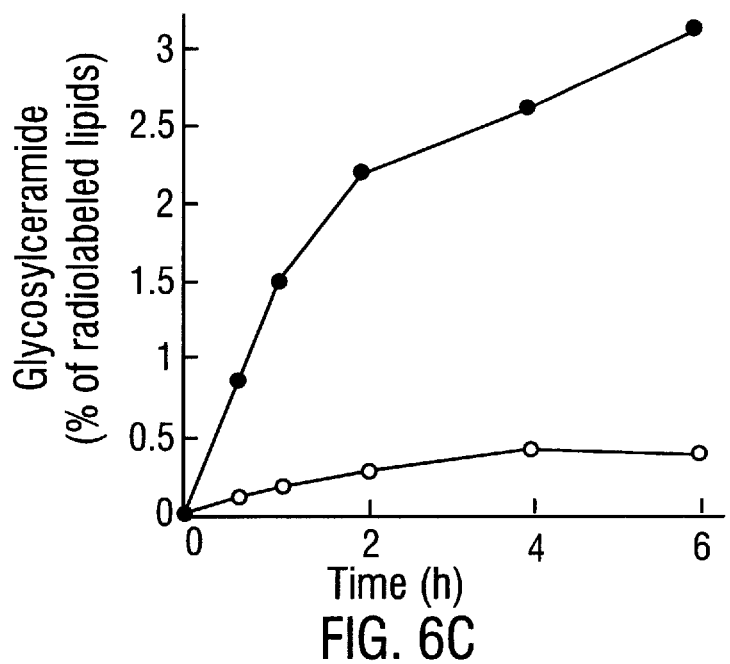

The incorporation of [$^3$H]palmitic acid into lipid-1 and -2, hereafter termed glycosylceramides, showed a strikingly different pattern. This diversity was characterized by a consistently higher rate of glycosylceramide formation in MCF-7-AdrR cells reaching a maximum of 3.1% of total lipid tritium at 6 h (FIG. 6C). In contrast, glycosylceramide formation in MCF-7-wt cells was significantly lower, accounting for only 0.38% of total lipid tritium at 6 h.

Taken together the data show an 8-fold difference in the rate of glycosylceramide formation in wt and MDR cell types. The rate of SM formation was found to be higher in MCF-7-AdrR cells compared to wt (approximately 2-fold). This difference may be due to enhanced ceramide formation in MCF-7-AdrR cells observed during short-term incubation with [$^3$H]palmitic acid.

These results are in agreement with previous work describing higher sphingomyelin levels (1.5-fold) in MDR cells compared to their drug sensitive parental cells (Ramu et al., 1984). The level of radiolabeled PC was found to be similar in both cells.

Example V

Mass Spectral Analysis of Lipid-1 and Lipid-2

In order to definitively establish structure, TLC-purified preparations of lipid-1 and -2 were analyzed by FAB/MS.

Figure 7A:
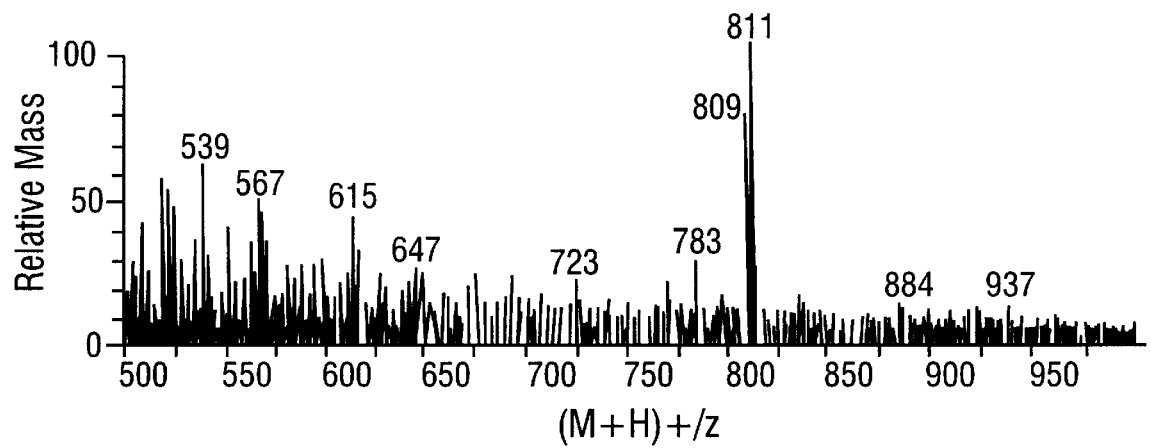
FIG. 7A and FIG. 7B. Fast-atom bombardment mass spectrometry of TLC-separated and purified lipids from MCF-7-AdrR cells. Each lipid band was characterized twice by both FAB-negative ion spectrometry and FAB-positive ion spectrometry. Representative FAB-positive samples are shown. Most probable identity of peaks is given in the text.

As shown in FIG. 7A, the upper band (lipid-1) was found to have a FAB/MS spectrum that is somewhat heterogeneous, although it appears to contain predominantly N-tetracosanoyl monoglycosylceramides in the cluster at (M+H)+/z 809/811 [precisely, N-tetracosanoyl (lignoceroyl) monoglycosylceramide at (M+H)+/z 811 and N-tetracosanoyl (nervonoyl) monoglycosylceramide at (M+H)+/z 809]. However, this band also contains peaks of (M+H)+/z 783 (N-docosanoyl), and 723 (N-linoleoyl) monoglycosylceramides.

In addition, the large breakdown peaks of (M+H)+/z 539 (N-palmitoyl ceramide), 567 (N-stearoyl ceramide), and 615 (N-docosanoyl ceramide) also suggest that this peak is more heterogeneous than the lower $R_f$ (lipid-2) peak. The heterogeneity and increased hydrophobicity of the lipid-1 peak, due to a larger inclusion of longer amide side chains, may account for its higher TLC migration.

Figure 7B:
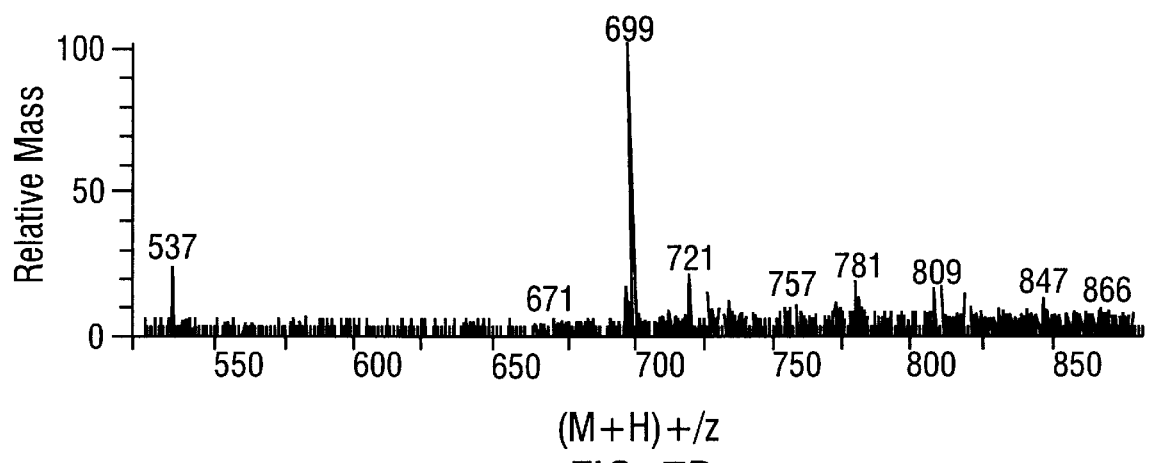

The lower TLC band (lipid-2) was found to have a FAB/MS spectrum highly characteristic of N-palmitoyl monoglycosylceramide. This is seen in FIG. 7B. The predominant peak of 699 is the native ion, with a well-defined N-palmitoyl ceramide breakdown peak of (M+H)+/z 537. This peak appears to be uniform, with a small content of other expected monoglycosylceramides with different amide chains [e.g., (M+H)+/z 721 (N-linolenoyl), 781 (N-docosaenoyl), and 809/811 (N-tetracosanoyl)]. The above analysis confirmed the existence of two major species of glycosylceramides, different in their fatty acid constituent, associated with MCF-7-AdrR cells.

Figure 8:
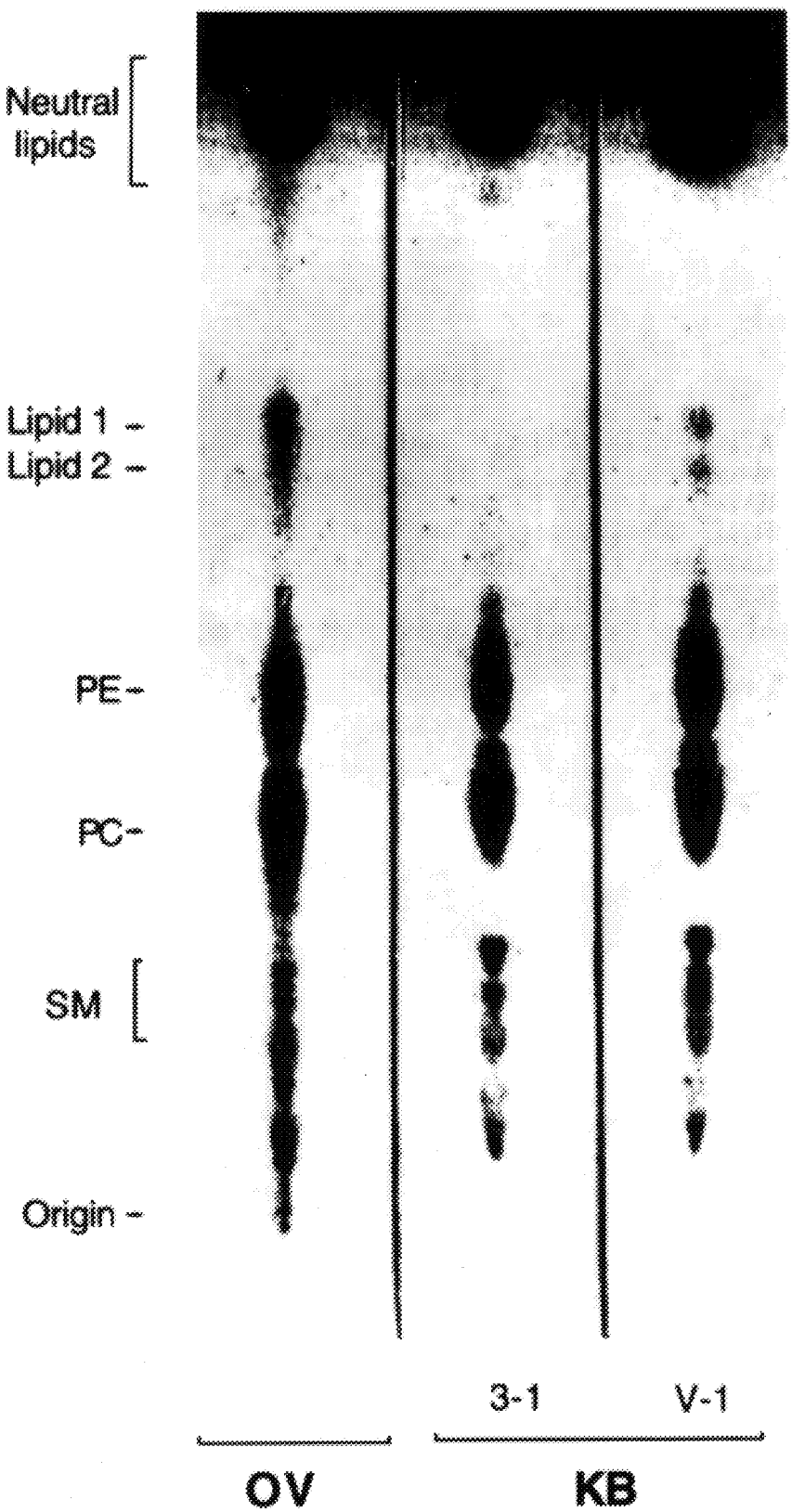
FIG. 8. Qualitative and quantitative analysis of lipids from wild-type and multidrug resistant cancer cells. Lipids were extracted from the cells as indicated in Example I. Equal amount of total lipid (50 $\mu$g/lane) was separated by TLC using solvent system I. The lipids were visualized and identified as described in the legend to FIG. 2. Abbreviations used: SM, sphingomyelin; PC, phosphatidylcholine; PE, phosphatidylethanolamine; OV, NIH:OVCAR-3 cells; 3-1, KB-3-1 cells; V-1, KB-V-1 cells.

In addition to MCF-7-AdrR cells, glycosylceramide accumulation was also observed in other MDR cells. FIG. 8 shows the lipid composition of OVCAR-3 (MDR ovarian carcinoma), and KB-3-1 (drug-sensitive, wt), and KB-V-1 (MDR) epidermoid carcinoma cells.

The MDR cells, OVCAR-3 and KB-V-1, most strikingly demonstrate the presence of the glycosylceramide doublet band. The ovarian carcinoma is known to be resistant to clinically relevant concentrations of adriamycin, melphalan, and cisplatin (Rogan et al., 1984). These data show that association of elevated glycosylceramide levels with MDR is more global as opposed to a biochemical characteristic of limited scope.

Example VI

Figure 9:
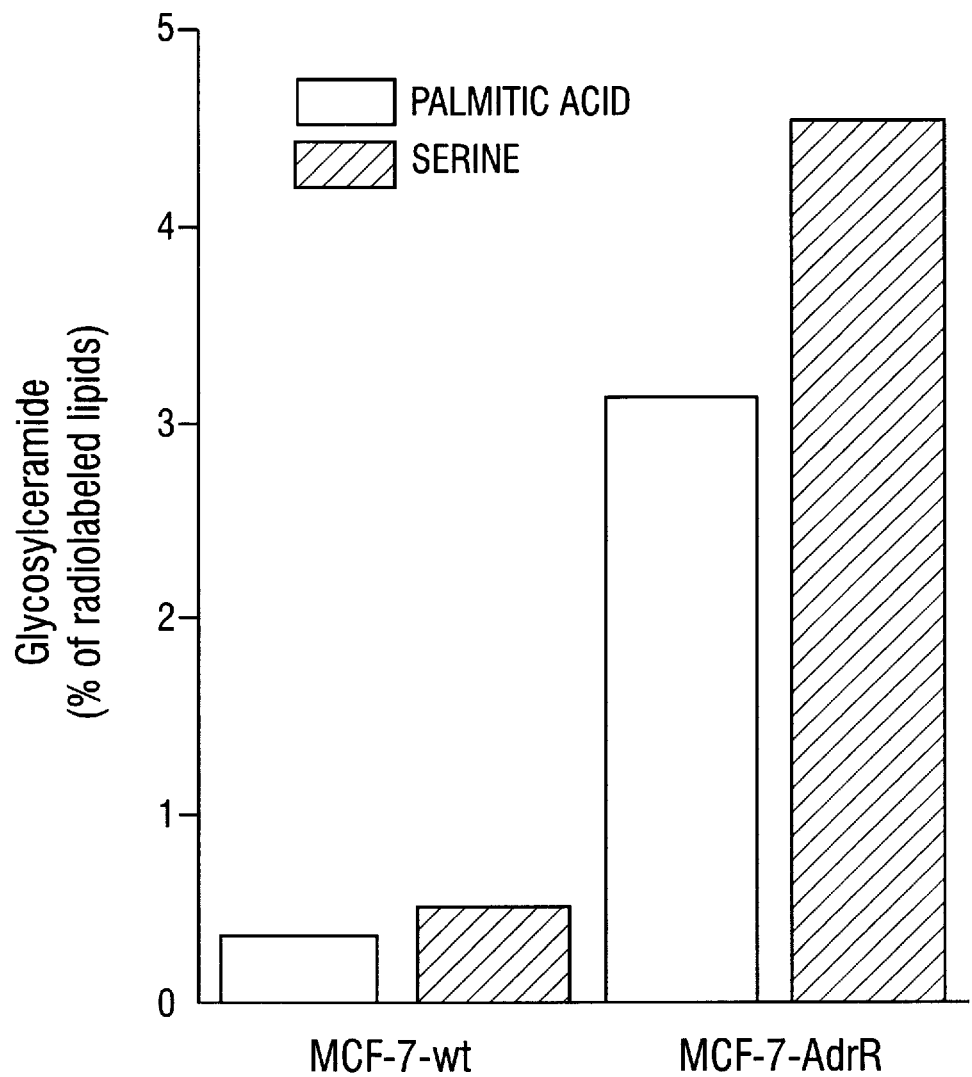
FIG. 9. Accumulation of glycosylceramide in MDR Cells. MCF-7-wt and MCF-7-AdrR cultures were labeled with 2.0 $\mu$Ci/ml [$^3$H]serine, or 1.0 $\mu$Ci/ml [$^3$H]palmitic acid for 24 h in RPMI-1640 medium containing 5% FBS. Cell lipids were extracted as described under Example I, and equal aliquots (by volume) were analyzed by TLC using solvent system I. Radiolabeled glycosylceramide, comigrating with commercial standard, was scraped from the plate, and quantitated by liquid scintillation spectrometry. Values represent the mean of determinations from three separate experiments, and are calculated as the percent glycosylceramide in the total lipid tritium extract. Uptake of radiolabeled precursors was similar in MCF-7-wt and MCF-7-AdrR cells reaching 0.8×10$^6$ and 0.88×10$^6$ cpm/dish for [$^3$H]serine, and 1.9×10$^6$ and 1.76×10$^6$ cpm/dish for [$^3$H]palmitic acid, respectively.

MDR Circumventing Drugs Inhibit Glycosylceramide Synthesis in Multidrug Resistant Cancer Cells Glycosylceramide accumulates in MDR cells (FIG. 9). In cells incubated with either [$^3$H]serine or [$^3$H]palmitic acid, [$^3$H]glycosylceramide consisted of 3–4.5% of total lipid tritium MCF-7-AdrR cells compared with 0.5% in MCF-7-wt cells. High levels of glycosylceramide have also been detected in other drug resistant cancer cells, showing that glycosylceramide accumulation is a general characteristic of MDR.

A major challenge in cancer chemotherapy is to understand the molecular mechanisms by which the so-called chemosensitizing drugs circumvent MDR. The effect of tamoxifen, the popular anti-estrogen and MDR reverser, on glycosylceramide metabolism in MCF-7-AdrR cells was investigated.

Figure 10:
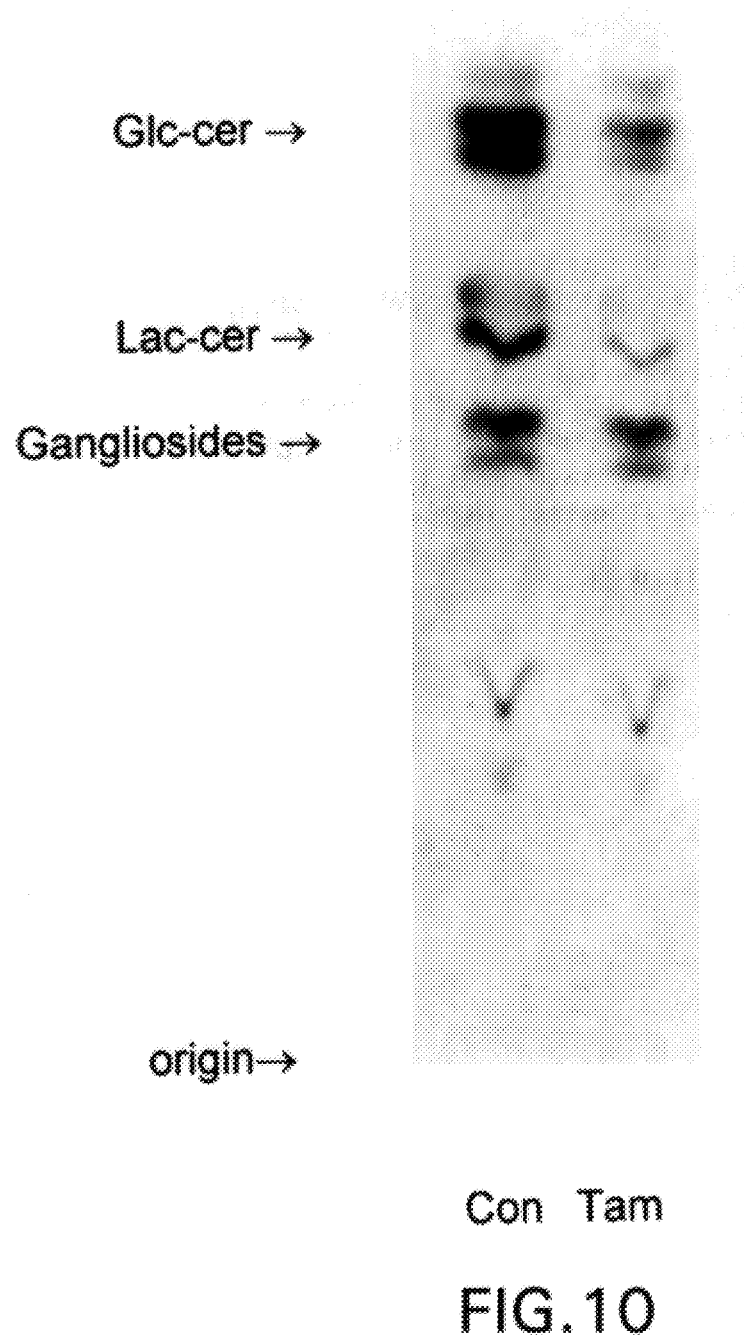
FIG. 10. Tamoxifen Inhibits Synthesis of Glycosphingolipids in MDR Cells. MCF-7-AdrR cultures, preincubated without or with 5.0 $\mu$M tamoxifen for 30 min, were then given 1.0 $\mu$Ci/ml [$^3$H]galactose for 24 h. Glycosphingolipids were analyzed as described under Example I, using equal aliquots of extracted lipids. The autoradiography of a representative chromatogram is shown. Glc-cer, glycosylceramide; Lac-cer, lactosylceramide; Con, control; Tam, tamoxifen.
Figure 17:
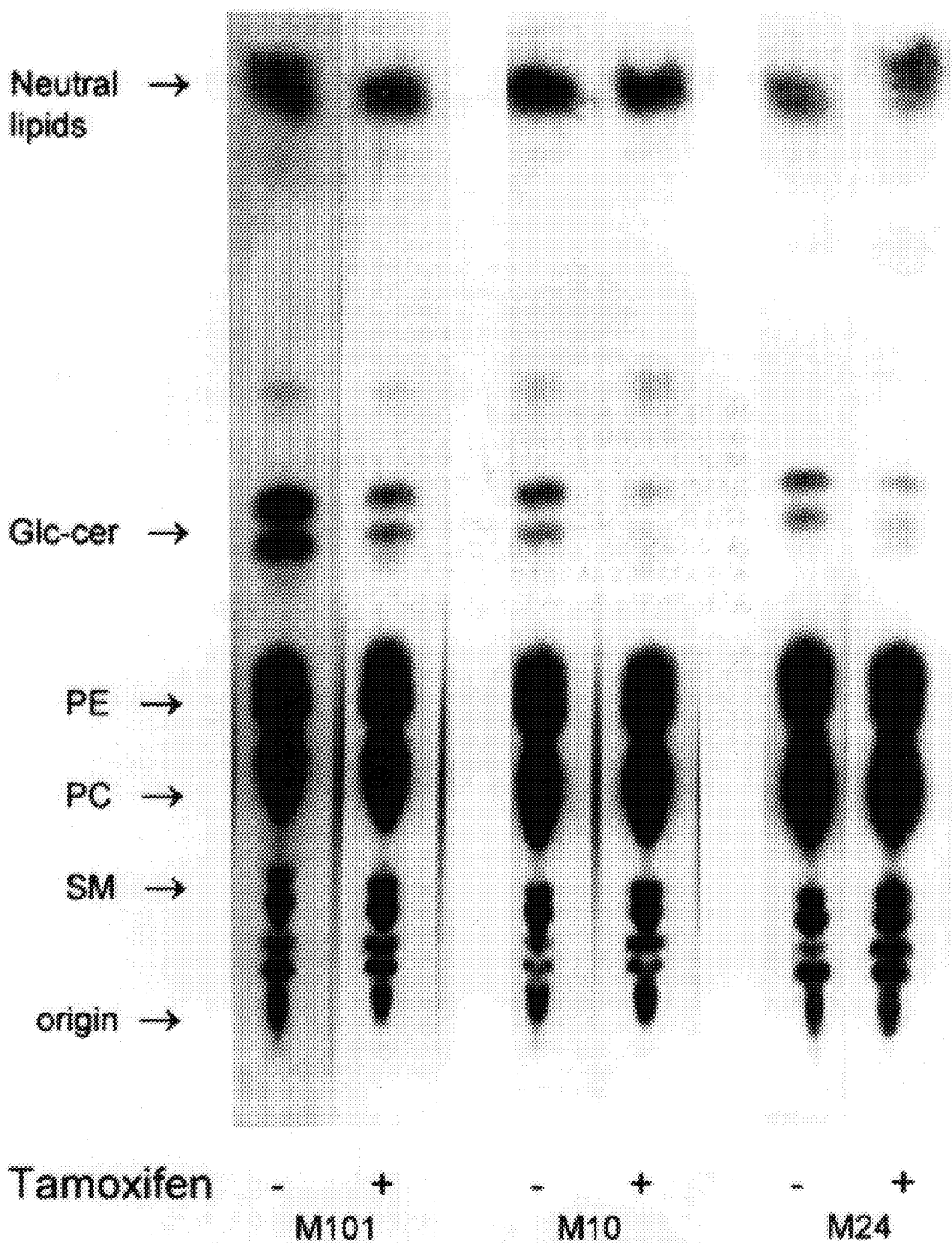
FIG. 17. Tamoxifen Inhibits Formation of Glycosylceramide in Human Metastatic Melanoma. The melanoma cells lines, M101, M10 and M24, were established from patient tumor specimens and cultured in the absence or presence of tamoxifen (5.0 μM) for 24 h with [$^3$H]palmitic acid (1.0 μCi/ml) in the medium. Identical aliquots of total lipid extract were applied to TLC, and the plate was exposed for autoradiography.
Figure 18:
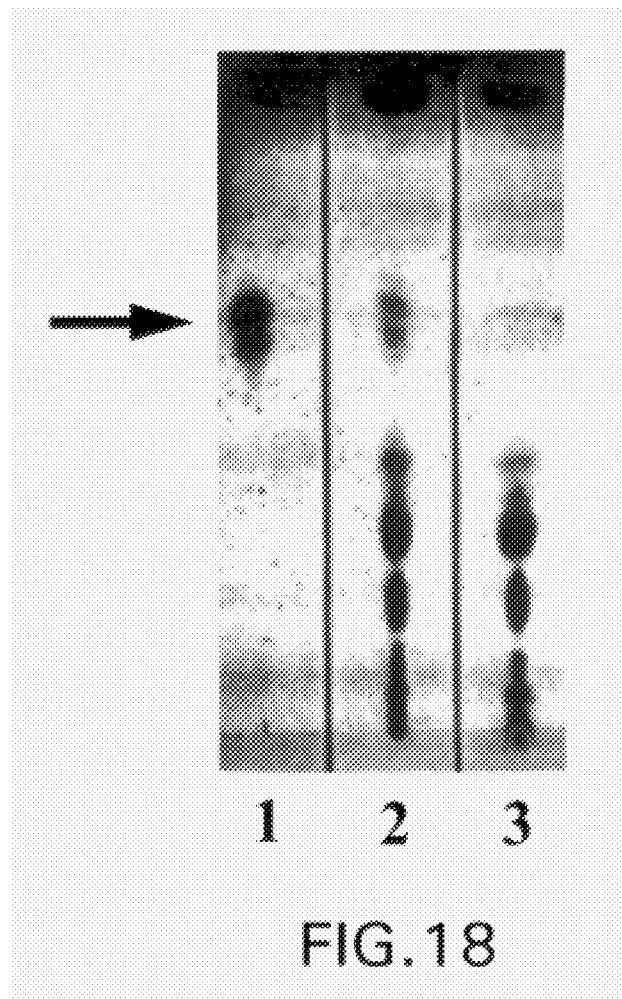
FIG. 18. Glycosylceramide is Elevated in Drug-Resistant Human Melanoma. Total lipids were extracted from human melanoma specimens (biopsy or surgery) and applied to TLC for analysis. Lane 1: glycosylceramide commercial standard; Lane 2: melanoma lipid (50 μg) from patient experiencing chemotherapy failure (drug resistant); Lane 3: melanoma lipid (50 μg) from patient who is chemotherapy naive.

For initial experiments, cells were preincubated with [$^3$H]galactose, minus or plus tamoxifen in the medium, and the extent of glycosphingolipid synthesis was surveyed by TLC autoradiography. As shown in FIG. 10, tamoxifen treatment caused inhibition in the synthesis of all major glycosphingolipids, reducing glycosylceramide, lactosylceramide and ganglioside levels by 69, 74, and 33%, respectively. Tamoxifen treatment also caused inhibition of glucosylceramide formation in three human melanoma cell lines derived from patient biopsies. FIG. 17. This observation is highly relevant in light of the additional finding that melanoma biopsies from patients treated with chemotherapeutic reagents have elevated glycosylceramide levels. FIG. 18.

Figure 11A:
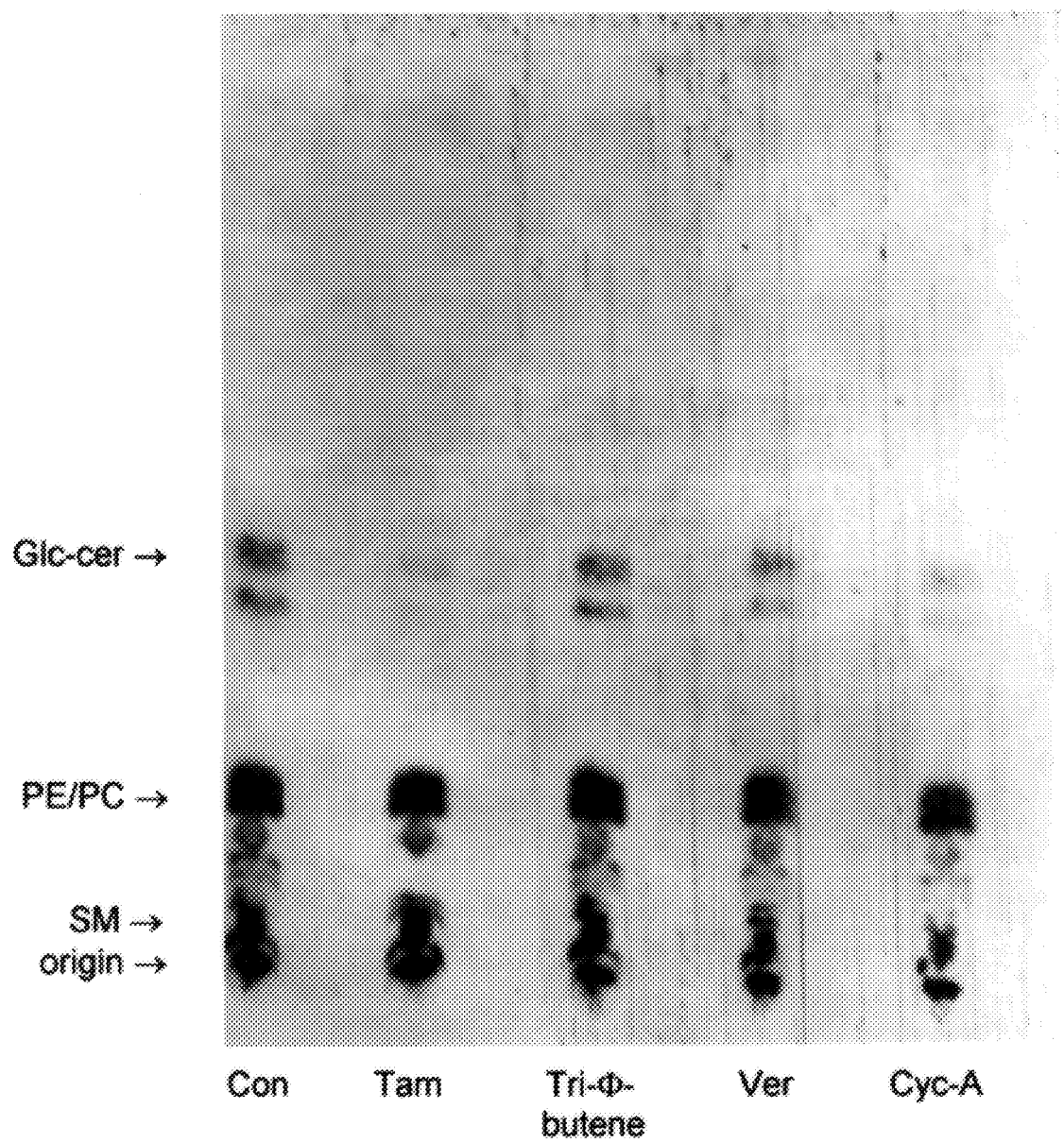
FIG. 11A and FIG. 11B. MDR reversing Drugs Inhibit Glycosylceramide Formation in MCF-7-AdrR Cells.

In addition to tamoxifen, two well-characterized MDR reversing agents, verapamil, and cyclosporin A, as well as a structural analog of tamoxifen, triphenylbutene, which is devoid of the basic amino side chain were also used. FIG. 11A shows an autoradiograph of a lipid extract from MCF-7-AdrR cells that had been preincubated with [$^3$H]serine. Radioactivity comigrated with sphingomyelin, phosphatidylcholine, phosphatidylethanolamine, and the glycosylceramide doublet.

Figure 11B:
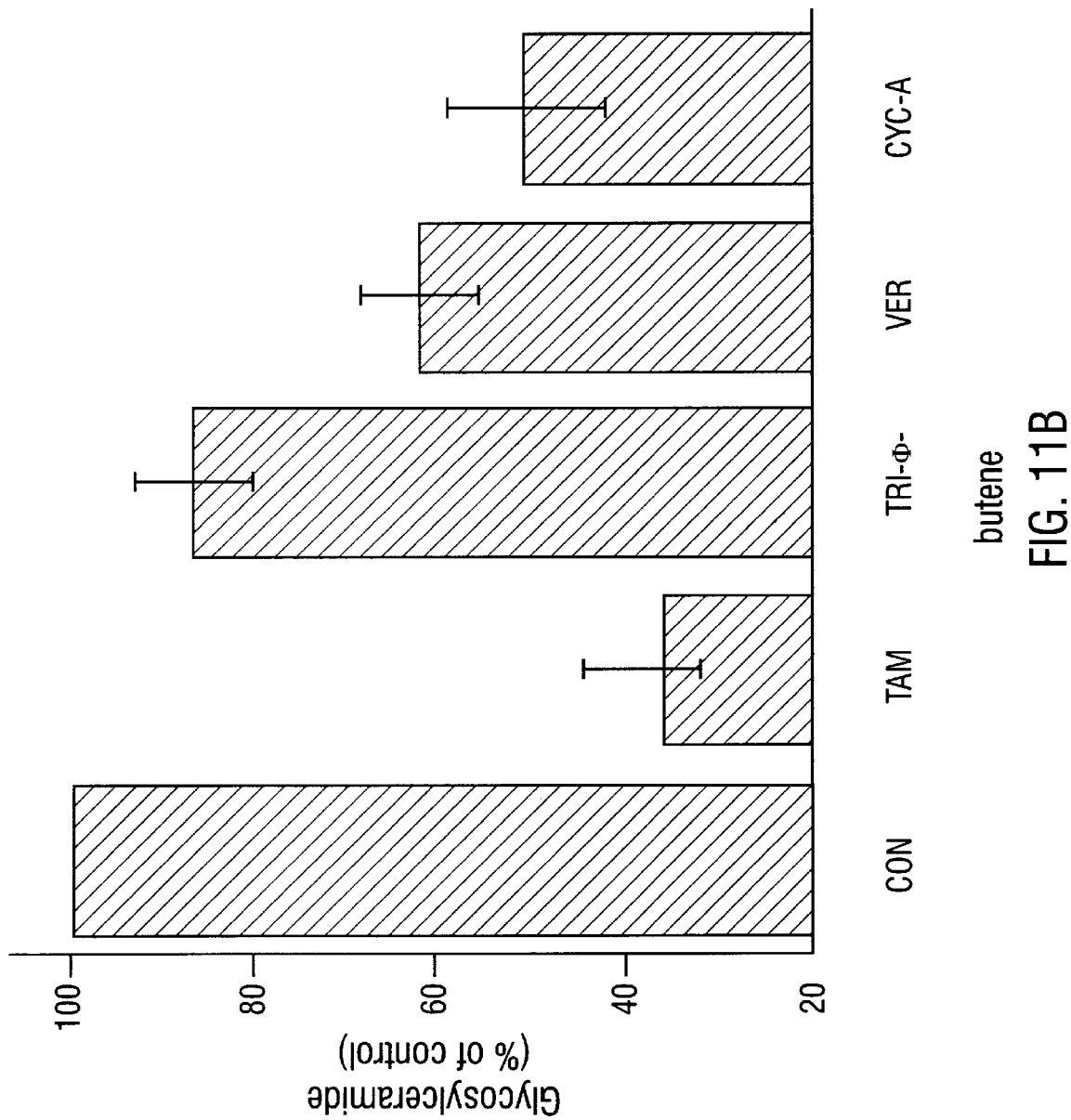

The autoradiograph shows that [$^3$H]glycosylceramide synthesis was extensively inhibited by all MDR reversing drugs, but not by the tamoxifen analog, triphenylbutene. FIG. 11B shows, based on cpm tritium, that the order of potency for inhibition of glycosylceramide formation in intact cells is tamoxifen>cyclosporin A≧verapamil (65, 49, and 38% inhibition, respectively).

Triphenylbutene had only a minor inhibitory effect (13% inhibition), indicating that the basic amino side chain is essential for tamoxifen action as an inhibitor or glycolipid metabolism. Inhibition of glycosylceramide formation by agents that circumvent MDR, which we observed in MCF-7-AdrR cells, is not restricted to this cell. Similar results have been obtained in KB-V-1 (vinblastine-resistant) epidermoid carcinoma cells, human melanoma, drug resistant ovarian carcinoma, cisplatin resistant breast cancer.

The classical MDR reversing agents have wide diversity in effective potency. The concentration dependence of the MDR reversing drugs for inhibition of glycosylceramide synthesis in MCF-7-AdrR cells was tested (FIG. 12). During a 24 h incubation with [$^3$H]palmitic acid, tamoxifen, verapamil, and cyclosporin A induced half-maximal inhibition (IC$_{50}$) of cellular [$^3$H]glycosylceramide formation at 1.0, 0.8, and 2.3 μM, respectively.

Tamoxifen was an efficient inhibitor of glycosylceramide formation, with the highest maximal effect and a low IC$_{50}$ value. Verapamil and cyclosporin A exhibit similar maximal inhibitory effects, with verapamil having a lower IC$_{50}$ value. The effective concentrations used herein are well within the range of clinical use, since treatment with these drugs typically results in 0.5–5 μM drug concentrations in serum of patients (Solary et al., 1991; Johnston et al., 1993; Slater et al., 1986b).

Figure 13A:
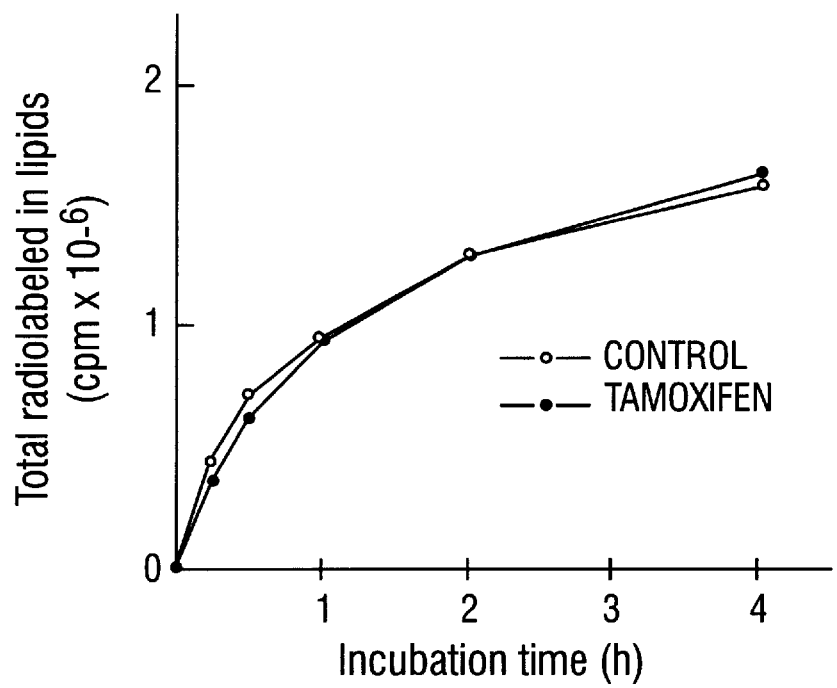
FIG. 13A, FIG. 13B and FIG. 13C. Temporal Pattern for the Influence of Tamoxifen on Total Lipid, Glycosylceramide, and Sphingomyelin Metabolism in MCF-7-AdrR Cells. Cells, preincubated in the absence or presence of tamoxifen (20 $\mu$M) for 30 min, were labeled by addition of 1.0 $\mu$Ci/ml [$^3$H]palmitic acid for the times shown using RPMI-1640 medium containing 5% FBS. At each time point, cultures were washed with PBS and lipids were extracted as described under Example I. Aliquots of the labeling medium were counted directly by liquid scintillation spectrometry to determine [$^3$H]palmitic acid uptake and incorporation into total cell lipids (FIG. 13A). Glycosylceramide (FIG. 13B) and sphingomyelin (FIG. 13C) levels were evaluated by TLC using solvent system I and II, respectively, followed by quantitation of radiolabel in the relevant regions as detailed in Example I. Results are the mean±SEM of duplicate determinations from two separate experiments.

The time-frame for tamoxifen-induced inhibition of glycosylceramide formation was also analyzed. As shown in FIG. 13A, uptake and incorporation of radiolabeled precursor ([$^3$H]palmitic acid) was very similar in control and tamoxifen-treated cells. This suggests that tamoxifen does not interfere with transport and overall utilization of palmitic acid by the cells.

Figure 13B:
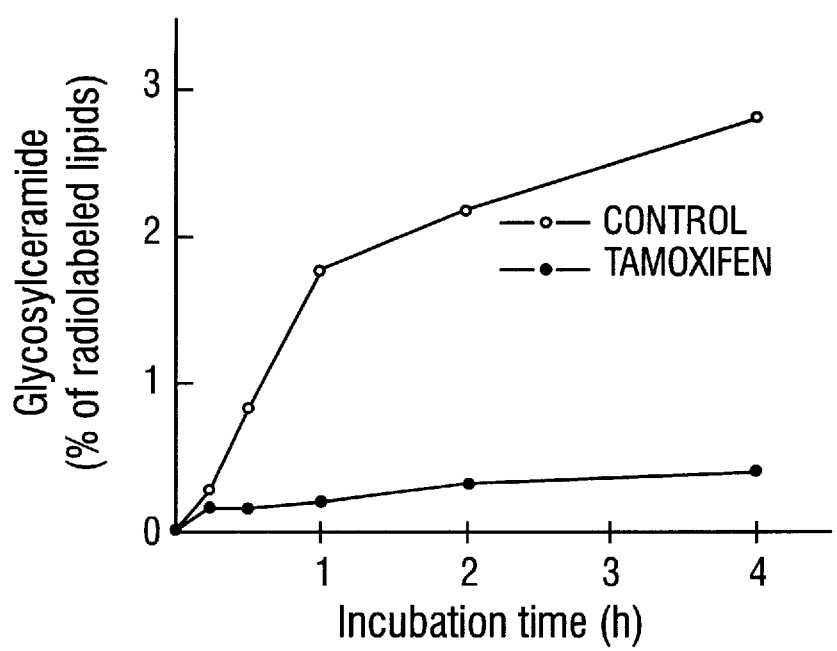
Figure 13C:
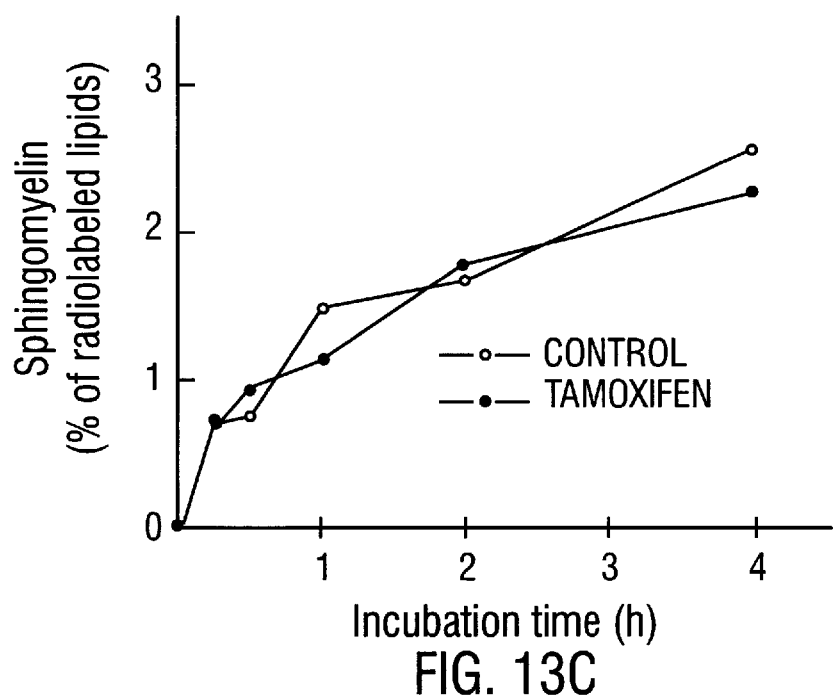

FIG. 13B, shows that tamoxifen specifically inhibits glycosylceramide formation starting as early as 15 min, with half-maximal influence at 45 min. In bold contrast, sphingomyelin synthesis was not altered by tamoxifen during the incubation period examined (FIG. 13C).

Figure 14A:
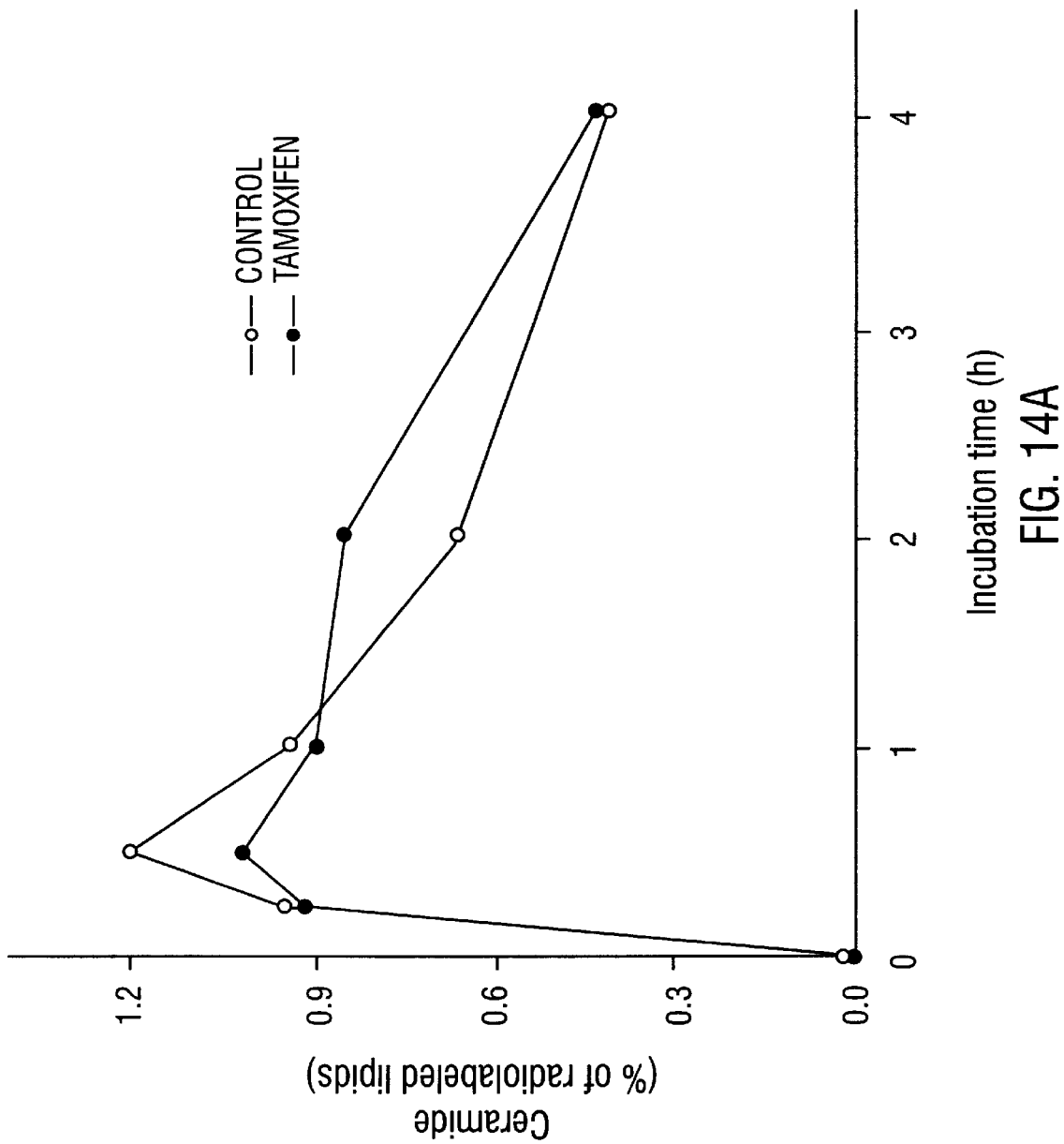
FIG. 14A and FIG. 14B. Effect of Tamoxifen on Ceramide Synthesis and Glycosylation in MCF-7-AdrR Cells.

Tamoxifen's inhibition of glycosylceramide synthesis may be a consequence of retarding the formation of metabolic precursors of glycosylceramide. To investigate this, the effect of tamoxifen on intracellular levels of ceramide, the primary precursor of all glycosphingolipids was analyzed. As shown in FIG. 14A, the level of ceramide was very similar in tamoxifen-treated and in tamoxifen-naive cells. Within the same 4 h time frame, glycosylceramide synthesis was almost completely inhibited by tamoxifen (FIG. 13B).

As tamoxifen did not alter ceramide or sphingomyelin formation, this raised the possibility that the drug effect is targeted to the glycosylation of ceramide, a reaction catalyzed by UDP-glucose:ceramide glucosyltransferase (Sweeley, 1985). In order to explore this notion, a short-chain ceramide analog with a 6-carbon N-acyl group ($C_6$-ceramide), was utilized as a substrate.

Figure 14B:
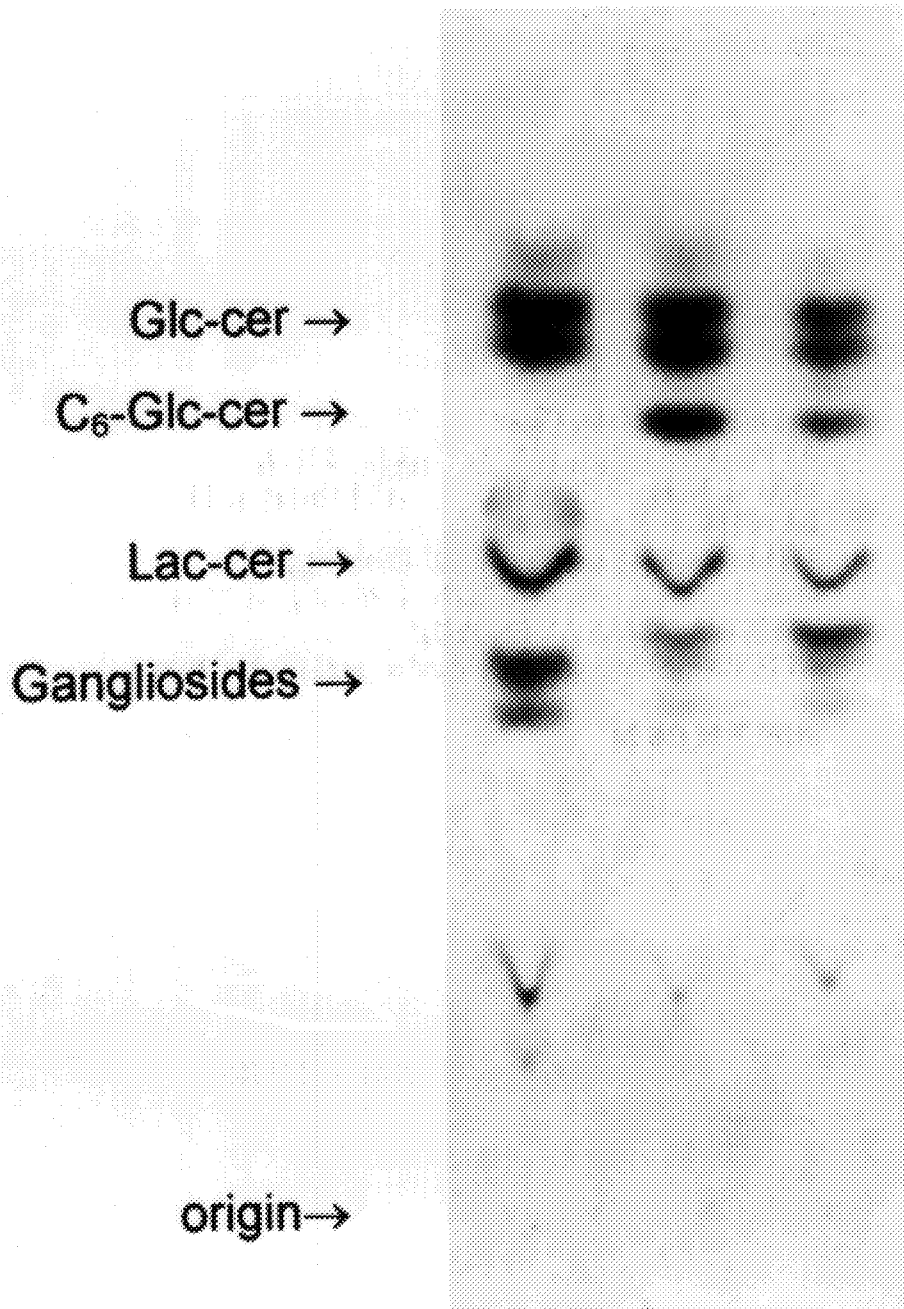

The short-chain analogs of ceramide are readily incorporated into cultured cells, and they have been widely used to identify the intracellular fate and biological activities of natural ceramide (Abe et al., 1992). FIG. 14B shows the intracellular spectrum of glycosphingolipids formed in the presence (middle lane) or absence (left lane) of $C_6$-ceramide. In the presence of $C_6$-ceramide, the synthesis of natural lacosylceramide and gangliosides was reduced by 33 and 35%, respectively, whereas the natural glycosylceramide level was not altered (middle lane).

The formation of $C_6$-glycosylceramide, migrating just below the natural glycosylceramide doublet, was clearly visible in extracts from cells incubated with $C_6$-ceramide. In the presence of tamoxifen (right lane), conversion of $C_6$-ceramide to $C_6$-glycosylceramide was inhibited by 54%. In addition, tamoxifen also inhibited the formation of natural glycosylceramide by 43% (right lane). These results show that tamoxifen inhibits ceramide glycosylation.

Example VII

Correlation Between Recovery of Adriamycin Toxicity and Reduction in Glycosylceramide Level in MCF-7-AdrR Cells The ability of tamoxifen to reverse MDR was evaluated by exposing MCF-7-AdrR cells to increasing concentrations of adriamycin in the absence or presence of a sublethal concentration of tamoxifen (or analog). The difference between toxicity elicited by adriamycin alone and toxicity of adriamycin in the presence of a given tested drug, reflects the potency of the drug to reverse MDR.

The effect of tamoxifen and triphenylbutene on adriamycin toxicity in MCF-7-AdrR cells is shown in FIG. 15A. In the presence of tamoxifen, the dose-response curve for adriamycin toxicity was shifted to lower concentrations. Maximal cytotoxic effect of adriamycin alone was achieved at 5 $\mu$M (28% cell death), while in the presence of tamoxifen, the same concentration of adriamycin (5 $\mu$M) caused 60% cell death.

This shows substantial enhancement in adriamycin toxicity. In contrast, triphenylbutene had no effect on adriamycin toxicity even at concentration as high as 5.0 $\mu$M (FIG. 15A). In order to learn whether the MDR reversing effect of tamoxifen was related to tamoxifen influence on glycosylceramide synthesis, [$^3$H]glycosylceramide levels were analyzed under the same conditions as the experiment in FIG. 15A.

Figure 15B:
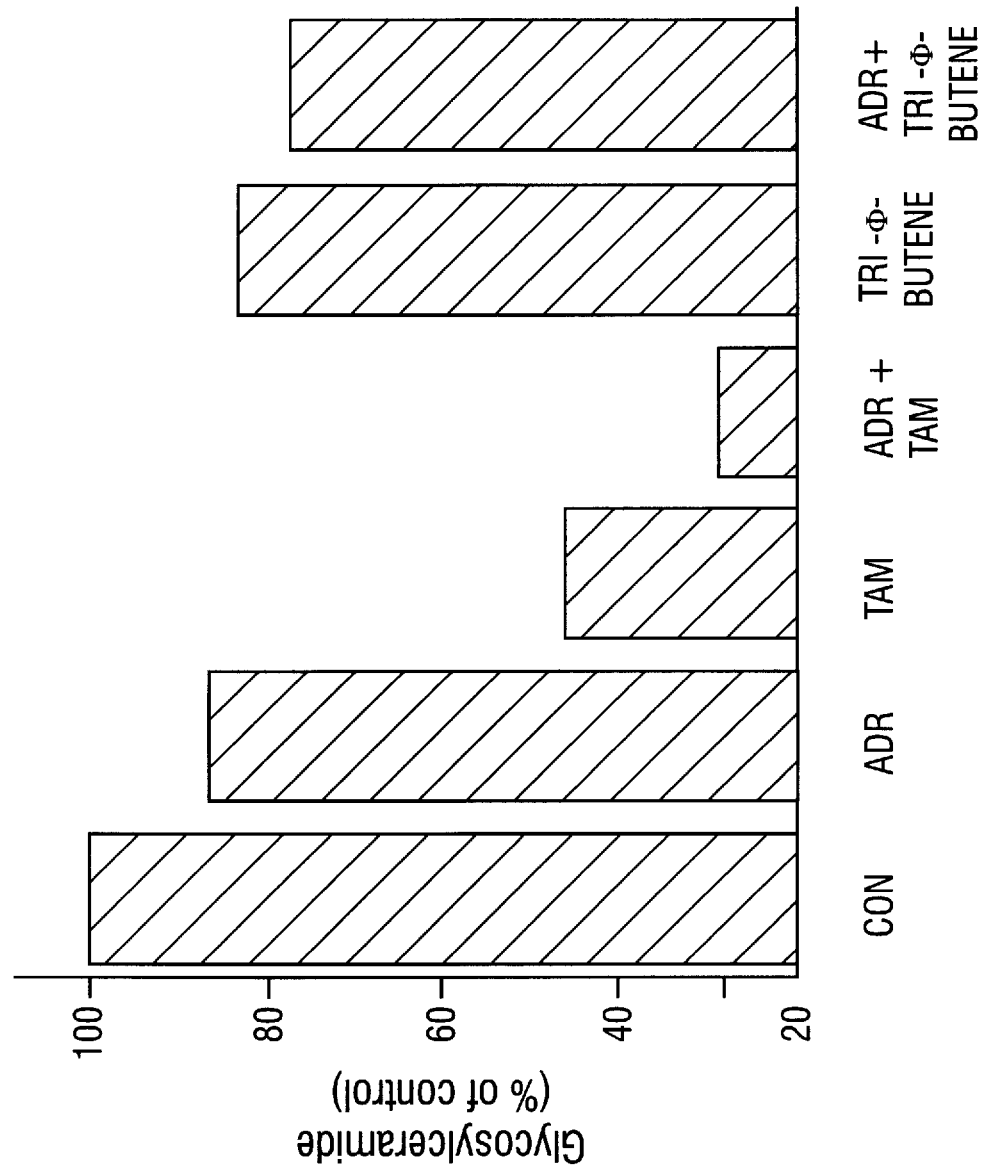

As shown in FIG. 15B, adriamycin, alone (2.5 $\mu$M), caused a minor diminution (17%) in glycosylceramide formation; this is similar with the minor effect of adriamycin (2.5 $\mu$M) on MCF-7-AdrR cell survival (FIG. 15A). Tamoxifen at 5.0 $\mu$M greatly retarded glycosylceramide synthesis (FIG. 15B, and former Figures) but by itself was not toxic to the cells (FIG. 15A). However, addition of tamoxifen to the adriamycin regimen caused 72% inhibition of glycosylceramide production (FIG. 15B), and together these agents were very potent in cell killing (FIG. 15A).

To substantiate the connection between chemosensitization and cellular glycosylceramide metabolism, triphenylbutene, a tamoxifen analog was used. When mixed with adriamycin, triphenylbutene did not enhance cell kill (FIG. 15A). FIG. 15B shows that triphenylbutene was not an effective inhibitor of glycosylceramide synthesis, either alone or in combination with adriamycin. These data strongly imply that glycosylceramide synthesis must be appreciably interrupted in order to have enhancement of adriamycin toxicity.

Example VIII

PPMP, a non-MDR Circumventory Agent, Sensitizes MCF-7-AdrR Cells to Adriamycin

The correlation between glycosylceramide content and modification of adriamycin toxicity in MDR cells was further investigated employing PPMP, an inhibitor of UDP-glucose:ceramide glucosyl-transferase. This inhibitor of glycosylceramide synthesis is well known for its specific actions, in a variety of cells (Inokuchi et al., 1987; Rani et al., 1995; Schwarz et al., 1995). Currently, however, there is no evidence that PPMP has any MDR reversing activity.

Figure 16A:
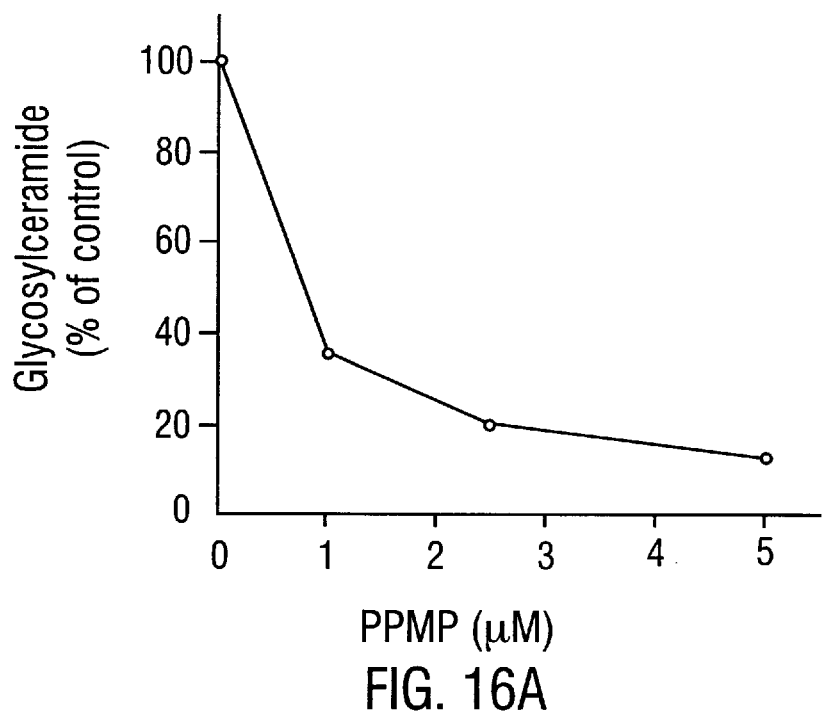
FIG. 16A and FIG. 16B. PPMP Inhibits Glycosylceramide Formation and Increases Sensitivity to Adriamycin Toxicity in MDR Cells.
Figure 16B:
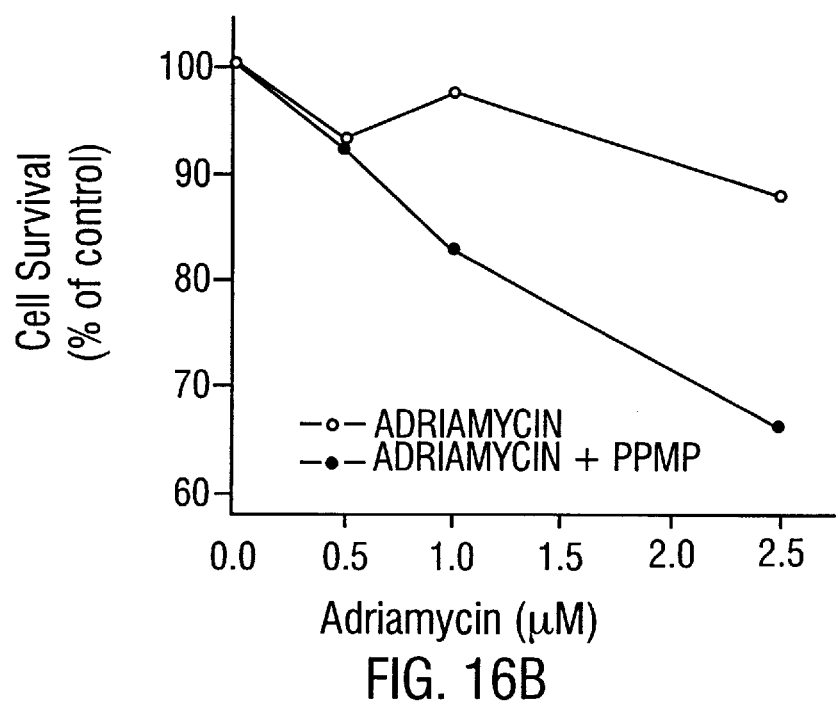

FIG. 16A shows the dose-response profile for PPMP effects on glycosylceramide synthesis, as examined in MCF-7-AdrR cells. Firstly, this enzyme inhibitor shows a strikingly similar dose-response relationship with tamoxifen (FIG. 12) for inhibition of glycosylceramide formation. Maximal reduction in cellular glycosylceramide levels (86% of control) occurred at 5.0 $\mu$M PPMP, with a calculated $IC_{50}$ of 0.9 $\mu$M. A concurrent effect of PPMP as chemosensitizer is revealed by the data of FIG. 16B, demonstrating an enhancement of adriamycin toxicity in MCF-7-AdrR cells. Whilst adriamycin was largely without influence on diminishing cell survival, the addition of PPMP to the adriamycin regimen effectively decreased cell survival. PPMP, alone, at the concentrations tested, had no effect on cell survival. Therefore, reduction of cellular glycosylceramide content, whether by MDR reverser (tamoxifen) or by an enzyme inhibitor (PPMP), resulted in cell chemosensitization to toxic insult by adriamycin.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abe, A., Radin, N. S., Shayman, J. A., Wotring, L. L., Zipkin, R. E., Sivakumar, R., Ruggieri, J. M., Carson, K. G., and Ganem, B. (1995). Structural and stereochemical studies of potent inhibitors of glucosylceramide synthase and tumor cell growth. J. Lipid Res. 36, 611–621.

Abe, A., Wu, D., Shayman, J. A., and Radin, N. S. (1992). Metabolic effects of short-chain ceramide and glucosylceramide on sphingolipids and protein kinase C. Eur. J. Biochem. 210, 765–773.

Al-Awqati, Q. (1995) *Science* 269, 805–806

Biedler, J. L., Chang, T. D., Meyers, M. B., Peterson, R. H. F., and Spengler, B. A. (1983). Drug resistance in Chinese hamster lung and mouse tumor cells. Cancer Treat. Rep. 67, 859–867.

Bligh, E. G., and Dyer, W. J. (1959) *Can. J Biochem. Physiol.* 37, 911–917

Blobe, G. C., Sachs, C. W., Khan, W. A., Fabbro, D., Stabel, S., Wetsel, W. C., Obeid, L. M., Fine, R. L., and Hannun, Y. A. (1993). Selective regulation of expression of protein kinase C (PKC) isoenzymes in multidrug-resistant MCF-7 cells. J. Biol. Chem. 268, 658–664.

Bose, R., Verheij, M., Haimovitz-Friedman, A., Scotto, K., Fuks, Z., and Kolesnick, R. (1995) *Cell* 82, 405–414

Bradley, G., and Ling, V. (1994). "P-glycoprotein, multidrug resistance and tumor progression." Cancer and Metastasis Rev. 13, 223–233.

Bradley, G., Juranka, P. F., and Ling, V. (1988). "Mechanism of multidrug resistance." Biochim. Biophys. Acta 948, 87–128.

Callaghan, R., and Higgins, C. F. (1995). Interaction of tamoxifen with the multidrug resistance P-glycoprotein. Br. J. Cancer 71, 294–299.

Cheresh, D. A., Harper, J. R., Schultz, G., and Reisfeld, R. (1984) *Proc. Natl. Acad. Sci. USA* 81, 5767–5771

Chin, K-V., Ueda, K., Pastan, I., and Gottesman, M. M. (1992) *Science* 255, 459–562

Cole, S. P. C., Bhardwaj, G., Gerlach, J. H., Mackie, J. E., Grant, C. E., Almquist, K. C., Stewart, A. J., Kurz, E. U., Duncan, A. M. V., and Deely, R. G. (1992) *Science* 258, 1650–1654

Doige, C. A., Yu, X., and Sharom, F. J. (1993). The effects of lipids and detergents on ATPase-active P-glycoprotein. Biochim. Biophys. Acta 1146, 65–72.

Dressler, K. A., Mathias, S., and Kolesnick, R. N. (1992) *Science* 255, 1715–1718

Fan, D., Beltran, P. J., and O'Brian, C. A. (1994). Reversal of multidrug resistance. In Reversal of Multidrug Resistance in Cancer, Kellen, J. A., editor, (CRC Press, Inc., Boca Raton, Fla.), pp. 93–127.

Freifelder, *PHYSICAL BIOCHEMISTRY*—2d Ed, W. H. Freeman & Co., 1982.

Fukuda, M. N., Dell, A., Tiller, P. R., Varki, A., Klock, J. C., and Fukuda, M. (1986) *J. Biol. Chem.* 261, 2376–2383

Furuya, S., Ono, K., and Hirabayashi, Y. (1995). Sphingolipid biosynthesis is necessary for dendrite growth and survival of cerebellar purkinje cells in culture. J. Neurochem. 65, 1551–1561.

Gottesman, M. M. (1993). How cancer cells evade chemotherapy: sixteenth Richard and Hinda Rosenthal Foundation award lecture. Cancer Res. 53, 747–754.

Gottesman, M. M., and Pastan, I. (1993) *Annu. Rev. Biochem.* 62, 385–427

Grabowski, G. A., Gatt, S., and Horowitz, M. (1990) Acid β-glucosidase: *Enzymology and Molecular Biology of Gaucher Disease*, CRC in Biochemistry and Molecular Biology 25, 384–414

Gupta, K. P., Ward, N. E., Gravitt, K. R., Bergman, P. J., and O'Brian, C. A. (1996). "Partial reversal of multidrug resistance in human breast cancer cells by N-myristoylated protein kinase C-α pseudosubstrate peptide." J. Biol. Chem. 271, 2102–2111.

Hakamori, S-I., (1993). "Structure and function of sphingolipids in transmembrane signaling and cell—cell interactions." Biochem. Soc. Trans. 21, 583–595.

Hakomori, S. (1981) *Annu. Rev. Biochem.* 50, 733–764

Hannun, Y. A., and Bell, R. M. (1989). Functions of sphingolipids and sphingolipid breakdown products in cellular regulation. Science 243, 500–507.

Harel, R., and Futerman, A. H. (1993). Inhibition of sphingolipid synthesis affects axonal outgrowth in cultured hippocampal neurons. J. Biol. Chem. 268, 14476–14481.

Holleran, W. M., DeGregorio, M. W., Ganapath, R., Wilbur, J. R., and Macher, B. A. (1986). Characterization of cellular lipids in doxorubicin-sensitive and -resistant P388 mouse leukemia cells. Cancer Chemother. Pharmacol. 17, 11–15.

Inokuchi J-I., Mason, I., and Radin, N. S. (1987). Antitumor activity via inhibition of glycosphingolipid biosynthesis. Cancer Lett. 38, 23–30.

Jaffrezou, J-P., Chen, G., Duran, G. E., Muller, C., Bordier, C., Laurent, G., Sikic, B. I., and Levade, T. (1995). Inhibition of lysosomal acid sphingomyelinase by agents which reverse multidrug resistance. Biochim. Biophys. Acta 1266, 1–8.

Jaffrezou, J-P., Herbert, J-M., Levade, T., Gau, M-N., Chatelain, P., and Laurent, G. (1991). Reversal of multidrug resistance by calcium channel blocker SR33557 without photoaffinity labeling of P-glycoprotein. J. Biol. Chem. 266, 19858–19864.

Johnston, S. R. D., Haynes, B. P., Sacks, N. P. M., McKinna, J. A., Griggs, L. J., Jarman, M., Baum, M., Smith, I. E., and Dowsett, M. (1993). Effect of estrogen receptor status and time on the intratumoral accumulation of tamoxifen and N-desmethyltamoxifen following short term therapy in human primary breast cancer. Breast Cancer Res. Treat. 28, 241–250.

Kellen J. A. (1996). Tamoxifen. Beyond the antiestrogen. Kellen, J. A., editor, (Birkhauser, Boston, Mass.).

Kirk, J., Syed, S. K., Harris, A. L., Jarman, M., Roufogalis, B. D., Stratford, I. J., and Carmichael, J. (1994). Reversal of P-glycoprotein-mediated multidrug resistance by pure anti-oestrogens and novel tamoxifen derivatives. Biochemical Pharmacol. 48, 277–285.

Lee, K. J., Boyd, S. A., and Radin, N. S. (1985) *Carbohydr. Res.* 144, 148–154

McClay, E. F., and McClay, M. E. T. (1994). Tamoxifen: is it useful in the treatment of patients with metastatic melanoma? J. Clin. Oncol. 12, 617–626.

Merrill, A. H. Jr., and Wang, E. (1986) *J. Biol. Chem.* 261, 3764–3769

Morton, D. L., Ravindranath, M. H., and Irie, R. F. (1994) *Prog. Brain Res.* 101, 251–275

Nakamura, S., Kozutsumi, Y., Sun, Y., Miyake, Y., Fujta, T., and Kawasaki, T. (1996). Dual roles of sphingolipids in signaling of the escape from and onset of apoptosis in a mouse cytotoxic T-cell, CTLL-2. *J Biol. Chem.* 271, 1255–1257.

Nayfield, S. G. (1995). Tamoxifen's role in chemoprevention of breast cancer: an update. *J. Cell. Biochem.* 22, 42–50.

Nilsson, O., and Svennerholm, L. (1982). Accumulation of glucosylceramide and glucosylsphingosine (psychosine) in cerebrum and cerebellum in infantile and juvenile Gaucher disease. *J. Neurochem.* 39, 709–718.

Obeid, L. M., Linardic C. M., Karolak, L. A., and Hannun, Y. A. (1993). Programmed cell death induced by ceramide. *Science* 259, 1769–1771.

Olivera, A., Buckley, N. E., and Spiegel, S. (1992) *J. Biol. Chem.* 267, 26121–26127

Ramu, A., Glaubiger, D., and Weintraub, H. (1984). Differences in lipid composition of doxorubicin-sensitive and -resistant P388 cells. *Cancer Treat. Rep.* 68, 637–641.

Rani, C. S. S., Abe, A., Chang, Y., Rosenzweig, N., Saltiel, A. R., Radin, N. S., and Shayman, J. A. (1995). Cell cycle arrest induced by an inhibitor of glucosylceramide synthase. *J. Biol. Chem.* 270, 2859–2867.

Rogan, A. M., Hamilton, T. C., Young, R. C., Klecker, R. W., and Ozols, R. F. (1984) *Science* 224, 994–996

Rosenwald, A. G., and Pagano, R. E. (1994). Effects of the glucosphingolipid synthesis inhibitor, PDMP, on lysosomes in cultured cells. *J. Lipid Res.* 35, 1232–1240.

Ruetz, S., and Gros, P. (1994) *Cell* 77, 1071–1081

Sabbatini, A. R. M., Basolo, F., Valentini, P., Mattii, L., Calvo, S., Fiore, L., Ciardiello, F., and Petrini, M. (1994) *Int. J. Cancer* 59, 208–211

Sachs, C. W., Safa, A. R., Harrison, S. D., and Fine R. L. (1995). Partial inhibition of multidrug resistance by safingol is independent of modulation of P-glycoprotein substrate activities and correlated with inhibition of protein kinase C. *J. Biol. Chem.* 270, 26639–26648.

Schwarz, A., Rapaport, E., Hirchberg, K., and Futerman, A. H. (1995). A regulatory role for sphingolipids in neuronal growth. *J. Biol. Chem.* 270, 10990–10998.

Shimabuku, A. M., Nishimoto, T., Ueda, K., and Komano, T. (1992) *J. Biol. Chem.* 267, 4308–4311

Slater, L. M., Sweet, P., Stupecky, M., and Gupta, S. (1986). Cyclosporin A reverses vincristine and daunomycin resistance in acute lymphatic leukemia in vitro. *J. Clin. Invest.* 77, 1405–1408.

Slater, L. M., Sweet, P., Stupecky, M., Wetzel, M. W., and Gupta, S. (1986b). Cyclosporin A corrects daunorubicin resistance in Ehrlich ascites carcinoma. *Br. J. Cancer* 54, 235–238.

Solary, E., Velay, I., Chauffert, B. C., Bidan, J-M., Caillot, D., Dumas, M., and Guy, H. (1991). Sufficient levels of quinine in the serum circumvent the multidrug resistance of the human leukemic cell K562/ADM. *Cancer* 68, 1714–1719.

Sundaram, K. S., and Lev, M. (1984) *J. Neurochem.* 42, 577–581

Sweeley, C. C. (1985). Sphingolipids. In Biochemistry of Lipids and Membranes, D. E. Vance and J. E. Vance, eds. (Menlo Park, Calif.: Benjamin/Cummings Publishing Company, Inc.), pp. 361–403.

Taki, T., Hirabayashi, Y., Ishikawa, H., Ando, S., Kon, K., Tanaka, Y., and Matsumoto, M. (1986) *J. Biol. Chem.* 261, 3075–3078

Thurin, J., Thurin, M., Herlyn, M., Elder, D. E., Steplewski, Z., Clark, W. H. Jr., and Koprowski, H. (1986). GD2 ganglioside biosynthesis is a distinct biochemical event in human melanoma tumor progression. *FEBS Lett.* 208, 17–22.

Tsuruo, T., Lida, H., Tsukagoshi, S., and Sakurai. Y. (1981). Overcoming of vincristine resistance in P388 leukemia in vivo and in vitro through enhanced cytotoxicity of vincristine and vinblastine by verapamil. *Cancer Res.* 41, 1967–1972.

Vance, D. E., and Vance, J. E. (1985) *Biochemistry of Lipids and Membranes*, Benjamin/Cummings Publishing Company, Inc., Menlo Park, Calif.

Volm, M., Kastel, M., Mattem, J., and Efferth, T. (1993). Expression of resistance factors (P-glycoprotein, Glutathione S-transferase-$\pi$, and Topoisomerase II) and their interrelationship to proto-oncogene products in renal cell carcinomas. *Cancer* 71, 3981–3987.

Wadkins, R. M., and Houghton, P. J. (1993). The role of drug-lipid interactions in the biological activity of multidrug resistance. *Biochim. Biophys. Acta* 1153, 225–236.

Wang, E., Norred, W. P., Bacon, C. W., Riely, R. T., and Merrill, A. H. Jr. (1991) *J. Biol. Chem.* 266, 14486–14490

Watanabe, T., Tsuge, H., Oh-hara, T., Naito, M., and Tsuruo, T. (1995). Comparative study on reversal efficacy of SDZ PSC 833, cyclosporin A and verapamil on multidrug resistance in vitro and in vivo. *Acta Oncologica* 34, 235–241.

Welsh, C. J., Robinson, M., Warne, T. R., Pierce, J. H., Yea, G. C., and Phang, J. M. (1994). Accumulation of fatty alcohol in MCF-7 breast cancer cells. *Archives Biochem. Biophys.* 315, 41–47.

Welsh, C. J., Yea, G. C., and Phang, J. M. (1994) *Biochem. Biophys. Res. Commun.* 202, 211–217

Wright, L. C., Dyne, M., Holmes, K. T., and Moutford, C. E. (1985). Phospholipid and ether linked phospholipid content alter with cellular resistance to vinblastine. *Biochem. Biophys. Res. Commun.* 133, 539–545.

Wu, W. I., McDonough, V. M., Nickels, J. T., Ko, J., Fischl, A. S., Vales, T. R., Merrill, A. H. Jr., Carman, G. M. (1995) *J. Biol. Chem.* 270, 13171–13178

Yan, J. P., Ilsley, D. D., Frohlick, C., Steet, R., Hall, E. T., Kuchta, R. D., and Melancon, P. (1995). 3'-Azidothymidine (Zidovudine) inhibits glycosylation and dramatically alters glycosphingolipid synthesis in whole cells at clinically relevant concentrations. *J. Biol. Chem.* 270, 22836–22841.

Yusa, K., and Tsuruo, T. (1989). Reversal mechanism of multidrug resistance by verapamil, direct binding of verapamil to P-glycoprotein on specific sites and transport of verapamil outward across the plasma membrane of K562/ADM cells. *Cancer Res.* 49, 5002–5006.

What is claimed is:

1. A method of determining inhibition of multidrug resistance by a candidate substance comprising the steps of:
   (i) providing a multidrug resistant cell, wherein an elevated level of at least one glucosylceramide in said cell indicates multidrug resistance;
   (ii) contacting said cell with a candidate substance;
   (iii) incubating said cell;
   (iv) measuring the level, in said cell, of said glucosylceramide; and
   (v) comparing the level of said glucosylceramide in the cell of step (iii) with the level of said glucosylceramide in the cell of step (i), wherein a decrease in the level of said glucosylceramide in the cell of step (iii), as compared to the cell of step (i), indicates that said candidate substance is an inhibitor or the multidrug resistance.

2. The method of claim 1, wherein the glucosylceramide is selected from the group consisting of N-tetracosanoyl (lignoceroyl) monoglucosylceramide, N-tetracosanoyl (nervonoyl) monoglucosylceramide, N-docosanoyl monoglucosylceramide and N-lineoyl monoglucosylceramide.

3. The method of claim 2, wherein the glucosylceramide is N-tetacosanoyl (lignoceroyl) monoglucosylceramide.

4. The method of claim 2, wherein the glucosylceramide is N-tetracosanoyl (nervonoyl) monoglucosylceramide.

5. The method of claim 2, wherein the glucosylceramide is N-docosanoyl monoglucosylceramide.

6. The method of claim 2, wherein the glucosylceramide is N-lineoyl monoglucosylceramide.

7. The method of claim 1, wherein said measuring comprises chromatographic separation of the components of said cell.

8. The method of claim 7, wherein said chromatographic separation comprises thin layer chromatography, gas chromatography, high performance liquid chromatography, paper chromatography, affinity chromatorgraph or super-critical flow chromatography.

9. The method of claim 1, wherein said measuring comprises contacting the components of said cell with a first antibody that is immunoreactive with an epitope on said glucosylceramide.

10. The method of claim 9, further comprising contacting the antibody-component mixture with a second antibody that is immunoreactive with said first antibody.

11. The method of claim 1, wherein said multidrug resistant cell is a cancer cell.

12. The method of claim 11, wherein said multidrug resistant cancer cell is selected from the group consisting of lymphoma, melanoma, sarcoma, leukemia, retinoblastoma, hepatoma, myeloma, glioma, mesothelioma and carcinoma.

13. The method of claim 12, wherein said multidrug resistant cancer cell is lymphoma.

14. The method of claim 12, wherein said multidrug resistant cancer cell is melanoma.

15. The method of claim 12, wherein said multidrug resistant cancer cell is sarcoma.

16. The method of claim 12, wherein said multidrug resistant cancer cell is leukemia.

17. The method of claim 12, wherein said multidrug resistant cancer cell is retinoblastoma.

18. The method of claim 12, wherein said multidrug resistant cancer cell is hepatoma.

19. The method of claim 12, wherein said multidrug resistant cancer cell is myeloma.

20. The method of claim 12, wherein said multidrug resistant cancer cell is glioma.

21. The method of claim 12, wherein said multidrug resistant cancer cell is mesothelioma.

22. The method of claim 12, wherein said multidrug resistant cancer cell is carcinoma.

* * * * *

UNITED STATES PATENT AND TRADEMARK OFFICE
CERTIFICATE OF CORRECTION

PATENT NO.    :   5,885,786

DATED         :   March 23, 1999

INVENTOR(S)   :   Myles Cabot

It is certified that error appears in the above-identified patent and that said Letters Patent is hereby corrected as shown below:

In claim 1, at column 46, line 65, please delete "or", and insert the following therefore: --of--.

Signed and Sealed this

Twenty-eighth Day of September, 1999

*Attest:*

Q. TODD DICKINSON

*Attesting Officer*   *Acting Commissioner of Patents and Trademarks*